(12) United States Patent
Chow et al.

(10) Patent No.: US 6,389,317 B1
(45) Date of Patent: May 14, 2002

(54) MULTI-PHASIC MICROPHOTODETECTOR RETINAL IMPLANT WITH VARIABLE VOLTAGE AND CURRENT CAPABILITY

(75) Inventors: Vincent Chow, Hanover Park; Alan Y. Chow, Wheaton, both of IL (US)

(73) Assignee: Optobionics Corporation, Wheaton, IL (US)

( * ) Notice: Subject to any disclaimer, the term of this patent is extended or adjusted under 35 U.S.C. 154(b) by 0 days.

(21) Appl. No.: 09/539,399

(22) Filed: Mar. 31, 2000

(51) Int. Cl.$^7$ .................................................. A61N 1/18
(52) U.S. Cl. ...................................................... 607/54
(58) Field of Search ........................ 607/1–2, 53–54, 607/116, 148; 623/4.1, 6.63

(56) References Cited

U.S. PATENT DOCUMENTS

| | | |
|---|---|---|
| 2,760,483 A | 8/1956 | Tassicker |
| 3,594,823 A | 7/1971 | Collins |
| 3,628,193 A | 12/1971 | Collins |
| 3,766,311 A | 10/1973 | Boll |
| 3,848,608 A | 11/1974 | Leonard |
| 3,914,800 A | 10/1975 | Collins |
| 4,001,867 A | 1/1977 | Kravitz et al. |
| 4,211,474 A | 7/1980 | Le Goff |
| 4,251,887 A | 2/1981 | Anis |
| 4,272,910 A | 6/1981 | Danz |
| 4,551,149 A | 11/1985 | Sciarra |
| 4,600,004 A | 7/1986 | Lopez et al. |
| 4,601,545 A | 7/1986 | Kern |
| 4,628,933 A | * 12/1986 | Michelson .................... 607/53 |
| 4,679,572 A | 7/1987 | Baker, Jr. |
| 4,750,498 A | 6/1988 | Graham |
| 4,810,050 A | 3/1989 | Hooper |
| 4,832,202 A | 5/1989 | Newman et al. |
| 4,873,448 A | 10/1989 | Shirai |

(List continued on next page.)

FOREIGN PATENT DOCUMENTS

| | | |
|---|---|---|
| DE | OS 195 29 371 | 2/1997 |
| EP | 0 084 621 A2 | 11/1982 |
| EP | 0 233 789 | 2/1987 |
| EP | 0 501 904 A2 | 2/1992 |
| GB | 2 229 543 A | 9/1990 |

OTHER PUBLICATIONS

Article published in *Science News,* Feb. 2, 1974, vol. 105, No. 5, p. 105.
Article published in *Science,* Jul. 1981.

(List continued on next page.)

*Primary Examiner*—Kennedy Schaetzle
*Assistant Examiner*—Kristen Droesch
(74) *Attorney, Agent, or Firm*—Brinks Hofer Gilson & Lione

(57) ABSTRACT

A visible and infrared light powered retinal implant is disclosed that is implanted into the subretinal space for electrically inducing formed vision in the eye. The retinal implant includes a stacked microphotodetector arrangement having an image sensing pixel layer and a voltage and current gain adjustment layer for providing variable voltage and current gain to the implant so as to obtain better low light implant performance than the prior art, and to compensate for high retinal stimulation thresholds present in some retinal diseases. A first light filter is positioned on one of the microphotodetectors in each of the image sensing pixels of the implant, and a second light filter is positioned on the other of the microphotodetectors in the image sensing pixel of the implant, each of the microphotodetectors of the pixel to respond to a different wavelength of light to produce a sensation of darkness utilizing the first wavelength, and a sensation of light using the second wavelength, and a third light filter is positioned on a portion of the voltage and current gain adjustment layer that is exposed to light, to allow adjustment of the implant voltage and current gain of the device by use of a third wavelength of light.

23 Claims, 12 Drawing Sheets

U.S. PATENT DOCUMENTS

| | | | |
|---|---|---|---|
| 4,978,842 | A | 12/1990 | Hinton et al. |
| 5,016,633 | A | 5/1991 | Chow |
| 5,024,223 | A | 6/1991 | Chow |
| 5,109,844 | A | 5/1992 | de Juan, Jr. et al. |
| 5,130,528 | A | 7/1992 | Phillips, Jr. |
| 5,130,776 | A | 7/1992 | Popovic et al. |
| 5,159,927 | A | 11/1992 | Schmid |
| 5,223,728 | A | 6/1993 | Gempe |
| 5,256,882 | A | 10/1993 | Miyasaka |
| 5,338,991 | A | 8/1994 | Lu |
| 5,351,309 | A | 9/1994 | Lee et al. |
| 5,397,350 | A | 3/1995 | Chow et al. |
| 5,411,540 | A | 5/1995 | Edell et al. |
| 5,476,494 | A | 12/1995 | Edell et al. |
| 5,491,349 | A | 2/1996 | Komoto et al. |
| 5,556,423 | A | 9/1996 | Chow et al. |
| 5,648,655 | A | 7/1997 | Rostoker |
| 5,717,201 | A | 2/1998 | Lin et al. |
| 5,865,839 | A | 2/1999 | Doorish |
| 5,895,414 | A * | 4/1999 | Chow et al. .................. 607/54 |
| 5,895,415 | A | 4/1999 | Chow et al. |
| 5,935,155 | A | 8/1999 | Humayun et al. |
| 5,944,747 | A | 8/1999 | Greenberg et al. |
| 6,032,062 | A | 2/2000 | Nisch |
| 6,035,236 | A | 3/2000 | Jarding et al. |
| 6,230,057 | B1 * | 5/2001 | Chow et al. .................. 607/54 |

OTHER PUBLICATIONS

Abrams, Dr. Susan B., "Implanted photodiodes could restore lost vision", Biophotonics Research, 2 pages, 1997.

Ando, Haruhisa, et al. "Design Consideration and Performance of a New MOS Imagine Device", 6 pages, IEEE (1985).

Armington, J.C., Brigell, M., "Effects of Stimulus Location and Pattern Upon the Visually Evoked Cortical Potential and the Electroretinogram," *Int J. Neurosci*, 1981; 14:169–178.

Baylor, D.A., Fourtes, M.G.F., "Electrical Responses of Single Cones in the Retina of the Turtle," *J Physiol*, 1970; 207:77–92.

Bergmann–Schaeffer, "Lehrbuch der Experimentalphysik" (Textbook of Experimental Physics), vol. II, "Electricity and Magnetism" by Prof. Dr. –Ing. H. Gobrecht, 3 pp., (1971) plus translation.

Bobsch, M.D., Joseph M. and Grosser, Ph.D., Morton "Newer Repair at the AXOM Level: A Merger of Microsurgery and Microelectronics," VCH Publishers, Inc. (1967).

Boettner, E.A., Wolter, J.R., "Transmission of the Ocular Media," *Invest Ophthalmol*, 1962; 1:776–783.

Brady, G.S., Clauser, H.R., *Materials Handbook, Thirteenth Edition*, New York, McGraw–Hill, 1991; 739–740.

Brindley, G.S., "The Site of Electrical Excitation of the Human Eye," *J. Physiol*, 1955; 127–189–200.

Brindley, G.S., "Beats Produced by Simultaneous Stimulation of the Human Eye with Intermittent Light and Intermittent or Alternating Electric Current," *J. Physiol*, 1962; 164:156–167.

Brown, et al., "Monolithically Integrated 1 x 12 Array of Planar InGaAs/InP Photodiodes," *Journal of Lightwave Technology*, vol. LT–4, No. 3, Mar. 1986, pp. 283–286.

Chapin, D.M., et al., "A New Silicon p–n Junction Photocell for Converting Solar Radiation into Electrical Power," Letters to the Editor, Journal of Applied Physics, vol. 25, (Jan.–Dec., 1954).

Chow, A.Y., "Electrical Stimulation of the Rabbit Retina with Subretinal Electrodes and High Density Microphotodiode Array Implants," ARVO Abstracts, *Invest Ophthalmol Vis Sci*. 199334 (Suppl):835.

Curcio, C.A., Sloan, K.R., Kaliha, R.E., Hendrickson, A.E., "Human Photoreceptor Topography," *J of Comparative Neurology*, 1990; 292:497–523.

Dawson, W.W., Radtke, N.D., "The Electrical Stimulation of the Retina by Indwelling electrodes," *Invest Ophthalmol Vis Sci.*, 1997; 16:249–252.

Dowling, J.E., Ripps, H., Visual Adaptation in the Retina of the Skate, *J Gen Physiol*, 1970; 56:491–520.

Eagle, R.C., Lucier, A.C., Bernardino, V.B., et al., "Retinal Pigment Epithelial Abnormalities in *Fundus Flavimaculatus*," *Ophthalmol*, 1980; 87:1189–1200.

Encyclopedia of Electronics, 2d Ed., Stan Gibilisco and Neil Sclater, Co–Editors–in–Chief, pp. 640–645 (1990).

Fenwick, P.B.C., Stone, S.A., Bushman, J., Enderby, D., "Changes in the Pattern Reversal Visual Evoked Potential as a Function of Inspired Nitrous Oxide Concentration," *Electroencephalogr Clin Neurophysiol*, 1984; 57178–183.

John B. Flynn, et al. "Total Active Area Silicon Photodiode Array", 3 pages (1964).

Graeme, J., "Position–Sensing Photodiode Amplifiers," Ch. 10, 12 pages.

Granit, R., Helme, T., "Changes in Retinal Excitability Due to Polarization and Some Observatios on the Relation Between the Processes in Retina and Nerve," *J. Neurophysiol*, 1939; 2:556–565.

Hagins, W.A., Penn, R.D., Yoshikami, S., "Dark Current and Photocurrent in Retinal Rods," *Biophys J.*, 1970; 19:380–412.

Hergert, Karl, "Detectors: Expanded Photodetector Choices Pose Challenges for Designers", The Photonics Design and Applications Handbook (1996).

Humayun, M.S., Propst, R.H., Hickinbotham, D., deJuan E., Jr., Dagnelie G., "Visual Sensations Produced by Electrical Stimulation of the Retinal Surface in Patients with Ed–Stage Retinities Pigmentosa (RP)," ARVO Abstracts, *Invest Ophthalmol Vis. Sci.*, 1993; 34 (Suppl):835.

Humayun, M., Propst R., De Juan, E., et al., "Bipolar Surface Electrical Stimulation of the Vertebrate Retina," *Arch Ophthalmol*, 1994; 112:110–116.

Kataoka, "An Attempt Towards an Artificial Retina: 3–D IC Technology for an Intelligent Image Sensor," *Transducers '85: International Conference on Solid–State Sensors and Actuators* 1985, pp. 440–442.

Knighton, R.W., "An Electrically Evoked Slow Potential of the Frog's Retina. I. Properties of Response," *J. Neurophysiol*, 1975; 38–185–197.

Lin, Heng–Chih, et al., "The Verticle Integration of Crystalline NMOS and Amorphous Orientational Edge Detector" IEEE Briefs, 3 pages, (1992).

Melen, et al., "A Transparent Electrode CCD Image Sensor for a Reading Aid for the Blind," *IEEE Journal of Solid–State Circuits*, vol. SC–9, No. 2, Apr. 1974, pp. 41–48.

Narayanan, M.V., Rizzo, J.F., Edell, D., et al., "Development of a Silicon Retinal Implant: Cortical Evoked Potentials Following Focal Stimulation of the Rabbit Retina with Light and Electricity," ARVO Abstracts, *Invest Opthalmol Vis Sci.*, 1994; 35(Suppl): 1380.

Pagon, R.A., "Retinitis Pigmentosa," *Surv Ophthalmol.*, 1988; 33:137–177.

Paton, D., Goldberg, M.F., *Management of Ocular Injuries*, Philadelphia, W.B. Saunders Co., 1976; 134–135.

The Penguin Dictionary of Electronics, Editor: Valerie Illingworth, Carol Young Market House Books Ltd., pp. 410–413 (1988).

Potts, A.M., Inoue J., Buffum D., "The Electricity Evoked Response of the Visual System (EER)," *Invest Ophthalmol Vis Sci.*, 1968; 7:269–278.

Robblee, Lois S., Electrochemical Guidelines for Selection of Protocols and Electrode Materials for Neural Stimulation, ch. 2, Renner Learning Resource Center (undated).

Rovamo, J., Virsu, A., "An Estimation and Application of the Human Cortical Magnification Factor," *Exp Brain Res.*, 1979; 37:495–510.

Rubin, M.L., *Optics for Clinicians*, Gainsville, TRIAD Scientific Publishers, 1974; 119–123.

Shannon, R.V., "A Model of Safe Levels for Electrical Stimulation," *IEEE Tarns Biomed Eng.*, 1992; 39:424–426.

Smith, J., "Creating a Bionic Eye", ABC News, Nov. 5, 1998, 3 pp.

Stone, J.L., Barlow, W.E., Humayun, M.S., deJuan, E., Jr., Milam, A.H., "Morphometric Analysis of Macular Photoreceptor and Ganglion Cells in Retinas with Retinitis Pigmentosa," *Arch Ophthalmol*, 1992; 110:1634–1639.

Sze, S.M., "Physics of Semiconductor Devices", $2^{nd}$ Ed., A Wiley–Interscience Publication, John Wiley & Sons, (undated).

Tasman, E., ed. *Duane's Foundations of Clinical Ophthamology*, vol. 3, Philadelphia, Lippincott, 1992; chapter 13:20–25, chapter 60:1–112.

Terr, L.I., Linthicum, F.H., House, W.F., "Histopathologic Study of the Cochlear Nuclei After 10 Years of Electrical Stimulation of the Human Cochlea," *Am J Otol.*, 1988; 9:1–17.

Tomita, T., "Electrical Activity of Vertebrate Photoreceptor," *Q Rev. Biophys.*, 1970; 3:179–222.

Zrenner, Dr. Eberhart, The Development of Subretinal Microphotodiodes for Replacement of Degenerated Photoreceptors, *Ophthalmic Res.* pp. 269–280 (1997).

\* cited by examiner

US 6,389,317 B1

MULTI-PHASIC MICROPHOTODETECTOR RETINAL IMPLANT WITH VARIABLE VOLTAGE AND CURRENT CAPABILITY

FIELD OF THE INVENTION

The present invention relates to medical products that are implanted into the eye that can restore a degree of vision to persons with vision loss caused by certain retinal diseases.

BACKGROUND

A variety of retinal diseases cause vision loss by destruction of the outer retinal vasculature and certain outer and inner retinal layers of the eye. The inner retina is also known as the neuroretina. The outer retinal vasculature is comprised of the choroid and choriocapillaris, and the outer retinal layers are comprised of Bruch's membrane and retinal pigment epithelium. The outer portion of the inner retinal layer that is affected is the photoreceptor layer. Variable sparing of other inner retinal layers, however, may occur. These spared inner retinal layers include the layers of the outer nuclei, outer plexiform, inner nuclei, inner plexiform, amacrine cells, ganglion cells, and the nerve fibers. The sparing of these inner retinal layers allows electrical stimulation of one or more of these structures to produce sensations of formed images.

Prior efforts to produce vision by electrically stimulating various portions of the retina have been reported. One such attempt involved a disk-like device with retinal stimulating electrodes on one side and photosensors on the other side. The photosensor current was to be amplified by electronics (powered by an external source) within the disk to power the stimulating electrodes. The device was designed to electrically stimulate the retina's nerve fiber layer via contact upon this layer from the vitreous cavity. The success of this device is unlikely because it must duplicate the complex frequency modulated neural signals of a nerve fiber layer which runs in a general radial course with overlapping fibers from different portions of the retina. Accordingly, the device would not only have to duplicate a complex and yet to be deciphered neural signal, but would also have to be able to select appropriate nerve fibers to stimulate that are arranged in a non-retinotopically correct position relative of the incident light image.

Another attempt at using an implant to correct vision loss involves a device consisting of a supporting base onto which a photosensitive material, such as selenium, is coated. This device was designed to be inserted through an external sclera incision made at the posterior pole and would rest between the sclera and choroid, or between the choroid and retina. Light would cause an electric potential to develop on the photosensitive surface producing ions that would then theoretically migrate into the retina causing stimulation. However, because this device has no discrete surface structure to restrict the directional flow of the charges, lateral migration and diffusion of charges would occur thereby preventing an acceptable image resolution capability. Placement of the device between the sclera and choroid would also result in blockage of discrete ion migration to the photoreceptor and inner retinal layers. This is due to the presence of the choroid, choriocapillaris, Bruch's membrane and the retinal pigment epithelium layer, all of which would block passage of these ions. Placement of the device between the choroid and retina would still interpose Bruch's membrane and the retinal pigment epithelium layer in the pathway of discrete ion migration. As the device would be inserted into or through the highly vascular choroid of the posterior pole, subchoroidal, intraretinal and intraorbital hemorrhage would likely result along with disruption of blood flow to the posterior pole.

Another retinal stimulating device, a photovoltaic artificial retina device, is disclosed in U.S. Pat. No. 5,024,223. This patent discloses a device inserted into the potential space within the retina itself. This space, called the subretinal space is located between the outer and inner layers of the retina. The disclosed artificial retina device is comprised of a plurality of so-called surface electrode microphotodiodes ("SEMCPs") deposited on a single silicon crystal substrate. SEMCPs transduce light into small electric currents that stimulate overlying and surrounding inner retinal cells. Due to the solid substrate nature of the SEMCPs, blockage of nutrients from the choroid to the inner retina can occur. Even with fenestrations of various geometries, permeation of oxygen and biological substances is not optimal.

U.S. Pat. No. 5,397,350 discloses another photovoltaic artificial retina device. This device is comprised of a plurality of so-called independent surface electrode microphotodiodes (ISEMCPs) disposed within a liquid vehicle, for placement into the subretinal space of the eye. The open spaces between adjacent ISEMCPs allow nutrients and oxygen to flow from the outer retina into the inner retina. ISEMCPs incorporate a capacitive layer to produce an opposite direction electrical potential to allow biphasic current stimulation. Such current is beneficial to prevent electrolysis damage to the retina a due to prolonged monophasic stimulation. However, like the SEMCP device, the ISEMCP depends upon light from the visual environment to power it, and so the ability of this device to function in low light environments is limited. The ISEMCP also does not provide a way to address localized variations in the sensitivity to electrical stimulation of surviving retinal tissue. Accordingly, there is a need for retinal implants that can operate effectively in low light environments and are capable of compensating for variations of retinal sensitivity within an eye.

BRIEF SUMMARY

In order to address the above needs, a retinal implant for electrically inducing formed vision in an eye, a so-called Variable Gain Multiphasic Microphotodiode Retinal Implant (VGMMRI) is disclosed capable of producing positive or negative polarity stimulation voltages and current both of greater amplitude in low light environments than the previous art. The increased voltage and current will be called gain.

According to one aspect of the invention, the retinal implant (also referred to herein as a VGMMRI) includes multiple microphotodetector pairs arranged in columns on the surface of a silicon chip substrate. Each microphotodetector pair in each column has a first microphotodetector and a second microphotodetector having opposite orientations to incident light so that a P-portion of the first PIN microphotodetector and a N-portion of the second NiP microphotodetector are aligned on a first-end on the surface of a column so that they are facing incident light. Similarly, the N-portion of the first PiN microphotodetector and a P-portion of the second NiP microphotodetector are aligned on a second-end that is opposite the first-end and directed towards the substrate. The microphotodetector pairs of each column are also arranged so that the P-portions and N-portions of both ends of all the microphotodetector pairs line up along the long axis of the column. A common retina stimulation electrode connects the first-end P- and N-portions of each microphotodetector pair. On the second-end, each column of microphotodetector pairs has a first contact strip in electrical contact with the second-end N-portions of all microphotodetectors in each column, and a second contact strip that is in electrical contact with the second-end P-portions of all microphotodetectors in the column. This same arrangement is repeated for all columns of microphotodetector pairs on the device. Thus, each column of microphotodetector pairs has two independent common second contact strips on the second-end extending the length of the column and beyond to the ends of two underlying strip-shaped photodiodes, one connecting all the second-end N-portions of all the overlying PiN microphotodetector pairs in the column, and the other connecting all the second-end P-portions of all the overlying NiP microphotodetector pairs in the column.

Beneath the column, the second-end N-portion common contact strip of the column is in electrical contact with the P-portion of a first underlying strip-shaped PiN photodetector, that extends the length of the column and then beyond at the ends of the column. The purpose of this first underlying strip-shaped PiN photodetector is to provide increased voltage and/or current to the PiN microphotodetectors in the overlying column via the second-end N-portion common contact strip. Similarly, the second-end P-portion common contact strip is in electrical contact with the N-portion of a second underlying strip-shaped NiP photodetector that extends the length of the column and then beyond at the ends of the column. The purpose of this second strip-shaped NiP photodetector is to provide increased voltage and/or current to the microphotodetectors in the overlying column via the second-end P-portion common contact strip.

In one embodiment, three types of light filters, each passing a different wavelength portion of visible through infrared light, are deposited, one each, on the first-end P portion of the PiN microphotodetectors, the first-end N portion of the NiP microphotodetectors, and the P and N portions of the light exposed ends of the first strip-shaped underlying PiN photodetector and the light exposed ends of the second strip-second underlying NiP photodetector.

According to a second aspect of the resent invention, a method of adjusting the stimulation voltage amplitude and polarity, and/or current of a retinal implant positioned inside the eye is disclosed. The method includes the steps of providing a light powered retinal implant, the VGMMRI, having an electrical output that can be adjusted in voltage polarity, voltage, and current amplitude by varying the intensity of three different wavelength portions of visible and infrared illuminating light directed onto the retinal implant. The three different wavelengths are provided from incident light and from a headset device for projecting different wavelengths into the eye. The headset device is modified Adaptive Imaging Retinal Stimulation System (AIRES) as described in U.S. Pat. No. 5,595,415, incorporated herein by reference, and modified to produce images and background illumination in three different wavelengths of visible and infrared light.

According to a third aspect of the present invention, a retinal implant is disclosed that is fabricated as separated individual VGMMRI microtile-like pixels each possessing at least one microphotodetector pair and one pair of underlying strip photodetectors, such that the microtile-like pixels are held in a mesh-like lattice. The open spaces between the pixels within the lattice allow nutrients and oxygen to permeate between the outer and inner retinal layers.

DETAILED DESCRIPTION OF THE PRESENTLY PREFERRED EMBODIMENTS

As described in further detail below, the present invention relates to a retinal implant that can vary its stimulation voltage polarity and also produce higher stimulation voltages and currents to the retina compared to retinal implants of the prior art. This higher and adjustable stimulation voltage and current allow for higher voltage and/or current stimulation thresholds that may be required to stimulate severely damaged retinal tissue. Although a preferred embodiment of the retinal implant disclosed below may be used on its own, without the need for any special stimulation apparatus positioned outside of the eye, in another embodiment the implant stimulation voltages and currents of the present invention are adaptable to the specific needs of a retina by the addition of regulated amounts of different wavelengths of projected images and background illumination light provided by a headset device that projects the different wavelengths into the eye. The use of this headset also allows the retinal implant to function in low light conditions.

Figure 1:
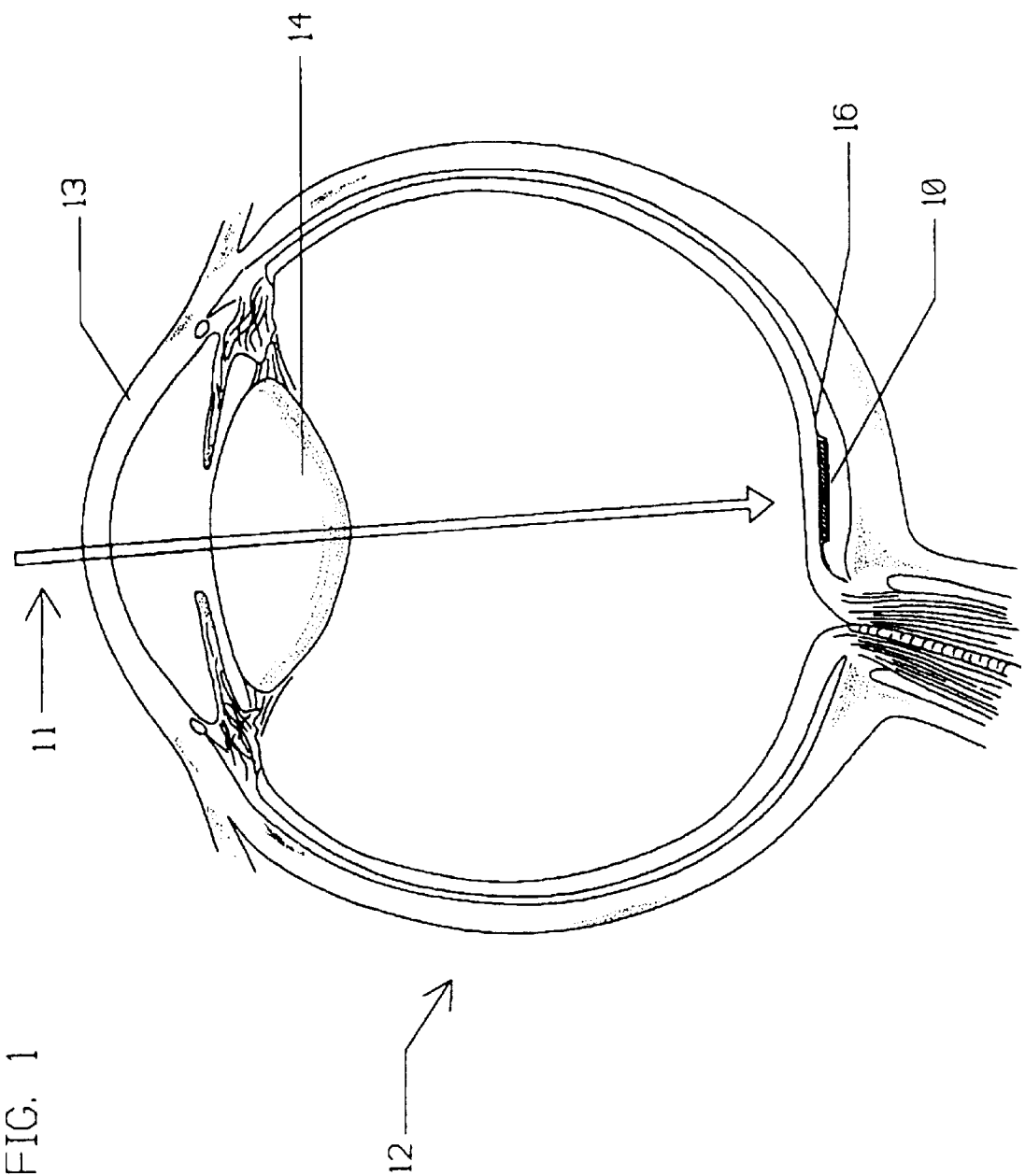
FIG. 1 is a simplified cross-sectional side view of an eye containing a VGMMRI retinal implant in the subretinal space.

As illustrated in FIG. 1, a retinal implant (also referred to herein as a variable gain multiphasic microphotodiode retinal implant or VGMMRI) 10 is positioned inside the eye 12, in the subretinal space 16, and is oriented to receive incident light 11 arriving through the cornea 13 and lens 14 of the eye 12. As used in this specification, the term light refers to visible and/or infrared light.

Figure 2:
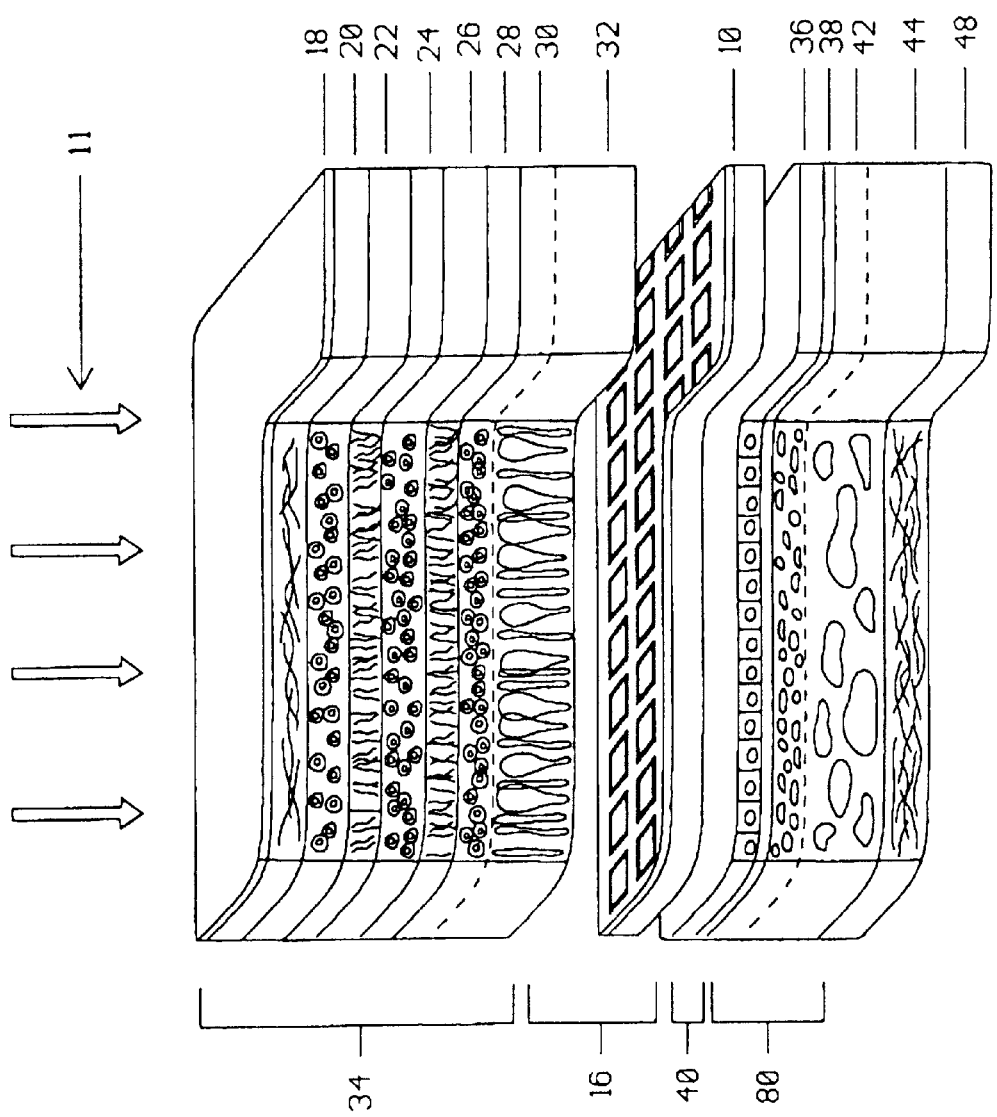
FIG. 2 is an enlarged exploded perspective sectional view of a portion of the retina illustrating a perspective sectional view of an embodiment of the VGMMRI in its preferred location in the subretinal space.

In FIG. 2, a high magnification perspective sectional view shows the VGMMRI 10 placed in its preferred position in the subretinal space 16. The layers of the retina from inside the eye to the outside in their respective positions are: internal limiting membrane 18; nerve fiber layer 20; ganglion and amacrine cell layer 22; inner plexiform 24; inner nuclear layer 26; outer plexiform 28; outer nuclear layer 30; and photoreceptor layer rod and cone inner and outer segments 32, all of which constitute the inner retina 34. It should be noted that the layers of the outer plexiform 28; outer nuclear layer 30; and photoreceptor layer rod and cone inner and outer segments 32 constitute the outer portion of the inner retina, but are sometimes referred to as just the "outer retina" in the art, although the meaning is clear to one skilled in the art as described in the above context. The VGGMRI 10 is disposed between the inner retina 34 and the outer retina 40 comprised of the retinal pigment epithelium 36 and Bruch'membrane 38. External to the outer retina 40 are the choriocapillaris 42 and choroidal vasculature 80 is the sclera 48.

Figure 3:
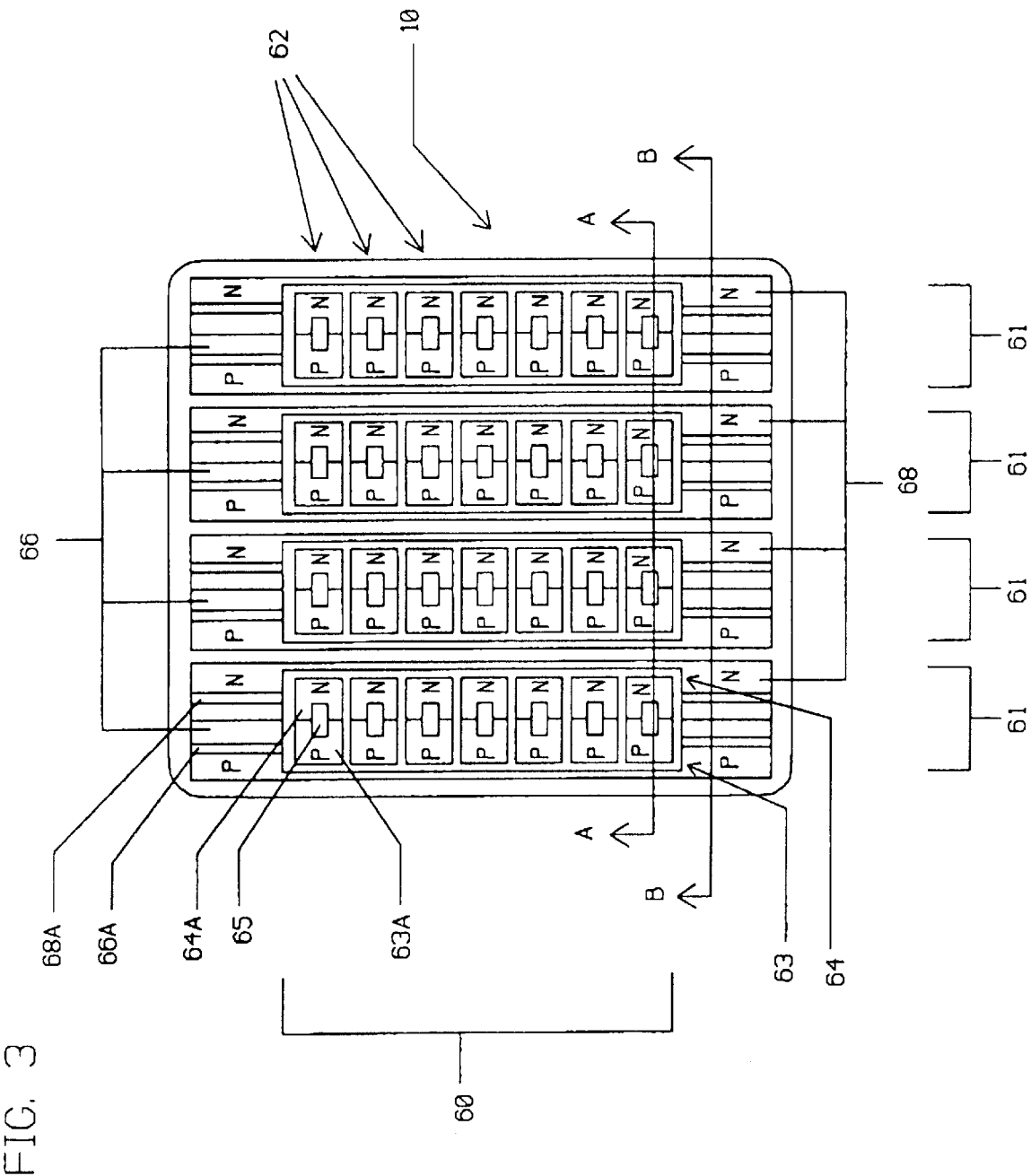
FIG. 3 is an incident-light-facing plan view of a VGMMRI according to a preferred embodiment of the present invention.
Figure 4:
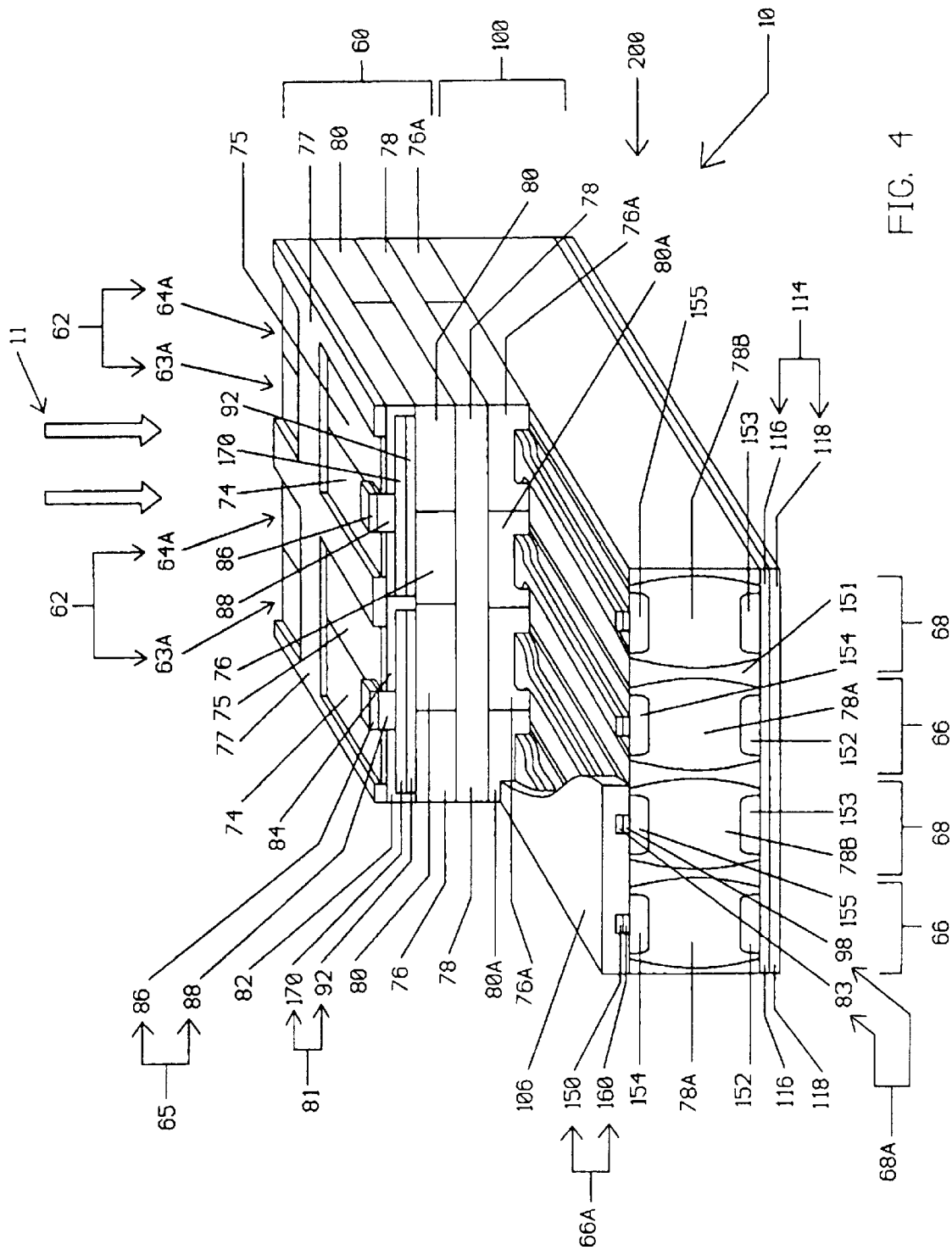
FIG. 4 is a portion of a perspective, stepped-sectional-view of the VGMMRI taken through sections A—A, and B—B of FIG. 3.

Referring to FIGS. 3 and 4, a preferred embodiment of a VGMMRI is shown. FIG. 3 is a incident-light-facing plan view of the VGMMRI 10 showing a top layer 60 of columns 61 of microphotodetector pairs 62, that are preferably microphotodiode pairs constructed from an amorphos silicon material and arranged on the surface of a underlying gain layer formed from a silicon chip substrate. The term microphotodetector, as used herein, is defined as any device capable of accepting light energy and converting it into an electrical signal, and/or current gain to the first strip-shaped PiN photodiode 66 that provides increased boltage and/or current gain to the first column 63 of the amorphous PiN microphotodetectors of the microphotodetector pairs 62 and a second strip-shaped NiP photodiode 68 that provides increase voltage and/or current gain to the second column 64 of the amorphous microphotodetectors pairs 62. Each amprphous PiN microphotodetector 63A and each amorphous NiP microphotodetector 64A of each mircophotodetector pair 62 has a common retinal stimulating electrode 65.

Beneath each microphotodetector column 61, the N-portion common contact strip 66A (FIG. 3) of the PiN microphotodetector column 63 is in electrical contact with the P-portion of a first underlying strip-shaped PiN photodetector 66. Also, the common contact strip 66A extends the length of the column 61 and then beyond to the ends of the P-portion of the first strip-shaped PiN photodiode 66. The purpose of this first underlying strip-shaped PiN photodetector 66 is to provide increased voltage and/or current gain to the overlying PiN microphotodetectors 63A.

Similarly, as best shown in FIG. 4, beneath the amporphous silicon microphotodetector column 61, the P-portion common contact strip 68A of the amorphous NiP microphotodetector column 64 (FIG. 3) is in electrical contact with the N-portion of the second underlying strip-shaped NiP photodetector 68. Also the common contact strip 68A extends the length of the column 61 and then beyond to the ends of the N-portion of the second strip-shaped NiP photodiode 68. The purpose of this second underlying strip-shaped Nip photodetector 68 is to provide increased voltage and/or current gain to the overlying amorphous NiP microphotodetectors 64A.

Although the VGMMRI 10 is preferably formed in the shape of a disc, other shapes including, but not limited to, rectangles, rings, portion of rings, irregular shapes, and other shapes may be fabricated to address the shape of the damaged retina to be stimulated. Also, in another embodiment of this invention shown in FIG. 4A, each VGMMRI pixel 62, each with its small section of underlying strip-shaped gain photodiodes 66, 68, (FIG. 4) may be fabricated as an individual pixel, physically separated in space from another pixel 62, but then commonly embedded in a lattice-like mesh 17 with other pixels 62. The purpose of this mesh structure is to allow nourishment to flow between the inner and outer retina through the channels of the mesh.

Referring again to FIG. 4, a stepped sectional view taken through a portion of the sections A—A and B—B of FIG. 3 further illustrates a preferred embodiment of the VGMMRI 10. FIG. 4 best shows the upper microphotodetector pixel layer 60 for receiving incident light images 11, and the voltage and/or current gain adjustment layer 100. The microphotodetector pixel layer 60 of the VGMMRI 10 is stacked on top of the voltage/current gain adjustment photodiode layer 100 and the two layers 60, 100 are electrically connected in series. Preferably, the microphotodetector pixels of the upper layer 60 are formed of an amorphous silicon material and the gain adjustment layer 100 is composed of photodetector strips formed of a crystalline silicon material. Additionally, the gain adjustment layer 100 preferably has a greater area than the area of the microphotodetector pixel layer 60 so that a portion of the gain adjustment layer 100 extends out beyond the perimeter of the microphotodetector layer 60. In one preferred embodiment, the upper microphotodetector layer 60 covers approximately 80% of the gain adjustment layer 100 and is centered on the gain adjustment layer 100 such that the portion of the gain adjustment layer extending beyond the perimeter of the microphotodetector layer 60 is exposed to incident light. In other embodiments, the gain adjustment layer 100 may also have the same area as microphotodetector layer 60; in this case, incident light 11 of a selected range of wavelengths pass through microphotodetector layer 60 to reach the lower gain adjustment layer 100. This result is achieved by taking advantage of the property of amorphous silicon to block certain wavelengths of visible light and pass certain wavelengths of infrared light.

The microphotodetector pixel layer 60 is made up of individual pixels 62 preferably constructed of an amorphous PiN 63A and an amorphous NiP 64A microphotodetector oriented so that the N portion 80 of each NiP microphotodetector 64A is adjacent the P portion 76 of each PiN microphotodetector 63A, and the P portion 76A of each NiP microphotodetector 64A is adjacent the N portion 80A of each PiN microphotodetector 63A. An intrinsic layer 78 is between the P portions and N portions of each microphotodetector 63A and 64A. The P portions 76, 76A, intrinsic layer 78, and N portions 80, 80A, of the microphotodetectors 63A and 64A are all preferably fabricated from amorphous silicon (a:Si), but may also be made from other photodetector materials well known to one skilled in the art. In another embodiment, the VGMMRI 10 may be fabricated by laminating two membranes of crystalline silicon (Silicon) microphotodetectors together to produce a similar structure to the preferred embodiment of this invention. This would be analogous to a multilayer PC board sandwiched together like a piece of plywood. The laminated membranes of crystalline silicon microphotodetectors would require interlayer connections and thin substrate 3-D silicon processing.

Both a Si/Silicon and Silicon/Silicon devices have their own advantages. Amorphous silicon can be used to fabricate a very thin device. Also, amorphous silicon and has strong light absorbing capability in the visible range which can add to the efficiency of photodetector devices made with this material. Crystalline silicon, however, possesses more desirable electrical leakage qualities than amorphous silicon that may prove advantageous in higher operating voltage implementations of a microphotodetector. This latter fact, however, is more of an issue with higher operating voltages than in self-biased operation. A laminated crystalline silicon structure can also produce very smooth pixel structures.

Referring again to FIG. 4, beginning with the point incident light 11 first reaches the surface of the VGMMRI, the specific structure of one preferred embodiment will be described. Layer 77 is a lattice-like light block fabricated from an opaque material, preferably a suitable thickness of platinum, that prevents cross-talk between pixels 62 of microphotodetector pairs. Each pixel 62 has electrode metallization 65 that connects adjacent PiN 63A and NiP 64A microphotodetectors. The formed inner electrode 81 electrically connects the P-side 76 of the PiN microphotodetector 63A with the adjacent N-side 80 of the NiP microphotodetector 64A. All PiN microphotodetectors 63A within the same column of pixels of FIG. 3, share a common lower electrode strip 150. Likewise all NiP photodetectors 64A within the same column of pixels 64 of FIG. 3, share a common lower electrode strip 83.

Continuing with FIG. 4, the upper electrode 65 has a first upper layer 86 of sputtered iridium/iridium oxide deposited on second upper layer 88 of platinum. The second upper layer 88 is deposited on a first inner layer 170 of platinum formed over a second inner layer 92 of titanium. The first inner platinum layer 170 is very thin and is semitransparent to light. It is deposited over another very thin second inner layer of semitransparent titanium 92 that forms a silicon adhesion layer to prevent titanium oxidation and to ensure proper surface conductivity. The second upper layer of platinum 88 is thicker and serves as the buildup metal for the final retinal stimulation electrode 65 completed by deposition of an iridium/iridium oxide layer 86 over the platinum layer 88. The formed inner electrodes 81; of microphotodetector pairs 62 are separated from each other by an insulating cap of silicon dioxide 82 having an opening for the retinal stimulation electrode 65.

The semitransparent titanium second inner layer 92 preferably contacts almost all of the surfaces of the adjacent P portion 76 and N portion 80 areas of the microphotodetectors 63A, 64A. It is noted that a metal contact surface is preferred that contacts as much of the active areas of each microphotodetector as possible to extract proper electrical current. This is because electron mobility can be limited in amorphous silicon and photon generated electrons in the depletion region may not travel far in the amorphous silicon material.

The PiN microphotodetector 63A in each microphotodetector pixel 62 includes, preferably, a visible-light pass filter 74 designed to allow a portion of visible light spectrum to pass through to excite the PiN-oriented microphotodetector 63A while blocking other wavelengths, including infrared light. In other embodiments, a light pass filter for other wavelengths of visible or infrared light would also be suitable. The NiP microphotodetector 64A of each microphotodetector pixel 62 includes preferably an infrared-light pass filter (IR-A) 75 to permit a portion of the infrared light spectrum to pass through to excite the NiP oriented microphotodetector 64A while blocking visible light. A suitable material for the IR-A pass filter 75 and the visible light pass filter 74 is an interference type filter material, although other filter types, well known to one skilled in the art, would also be suitable.

Although the embodiment of FIGS. 3 and 4 illustrate a microphotodetector pixel layer 60 with pixels 62 made up of paired PiN 63A and NiP 64A microphotodetectors having a particular structure, other types of multi-phasic microphotodetector retinal implant (MMRI) structures may be utilized. A detailed discussion of the various MMRI structures adaptable for use in the microphotodetector pixel layer 60 is presented in our U.S. Pat. No. 6,230,057 filed Mar. 26, 1998 and our U.S. Pat. No. 5,895,415 filed Jun. 6, 1995. The entire disclosure of each of these applications is incorporated herein by reference.

In the embodiment of FIGS. 3 and 4, the gain adjustment layer 100 has alternating columns of PiN 66 and NiP 68 voltage/current gain photodetector strips. Each PiN 66 and NIP 68 photodetector strip is preferably a single crystalline photodetector that spans the cord of the VGMMRI 10 at its particular position. A portion of all PiN 66 photodetector strips 66 is in electrical contact with the common platinum electrode strips 150 of the PiN columns of the amorphous microphotodetector pixel layer 60 via a titanium adhesion layer 160. Likewise, a portion of all NiP photodetector strips 68 are in electrical contact with the common platinum electrode strips 83 of the amorphous microphotodetector pixel layer 60 via a titanium adhesion layer 98.

In the embodiment shown in FIG. 4, a crystalline silicon substrate 200, which is an N properties substrate, is preferably the starting material of gain layer 100. The substrate 200 is fabricated on the top side (amorphous silicon side) with alternating P-doped (P+) strips 154 and N-doped (N+) strips 155. Similarly, the bottom side of gain layer 100 is processed with alternating N-doped (N+) strips 152 and P-doped (P+) strips 153, where N+ diffusion 152 is physically aligned with the P+ diffusion 154, and the P+ diffusion 153 is physically aligned with the N+ diffusion 155. Adjacent photodiode strips of PiN 66 and NiP 68 structures are isolated by N+ isolation channel 151 that penetrates the gain layer 100 from both sides, preferably merging in the middle of gain layer 100. Alternatively, trench isolation, which is well known to one skilled in the art, can also be used to isolate the photodiode strips 66, 68. The strips 66, 68 are aligned in parallel, in an alternating pattern, with the common electrode strips 150, 83 of the amorphous silicon microphotodetector layer 60. Each PiN crystalline silicon photodetector strip 66 is lined up with a respective column of PiN amorphous silicon microphotodetector pixel elements 63A above the common electrode strip 150, and each NiP crystalline silicon photodetector strip 68 is lined up with a respective column of NiP amorphous silicon pixel elements 64A above the common electrode strip 83. This matching alignment creates a desired series electrical connection of amorphous silicon pixels 63A, 64A with their respective silicon photodetectors 66, 68 in the gain adjustment layer 100.

The portions of the PiN and NiP strips 66, 68 extending past the perimeter edge of the microphotodetectors 62 are coated with an infrared-light pass filter (IR-B) 106. The IR-B filter 106 is preferably designed to pass a different bandwidth of infrared light than the IR-A filter 75 on the NiP microphotodetectors 64A of the amorphous silicon microphotodetector pixel layer 60. A bottom-side electrode 114, on the bottom side of the VGMMRI 10, preferably covers the entire bottom portion of the gain adjustment layer 100. The bottom-side electrode 114, which is preferably made of an iridium/iridium oxide coating 118 deposited over a titanium layer 116, extends over the entire bottom side of the VGMMRI 10 to allow even current distribution across the "ground" plane of the VGMMRI device 10. The bottom-side titanium layer 116 directly contacts all the P+ layers 153 and N+ layers 152. It is noted that the upper and lower electrodes 65, 114 of the VGMMRI 10 preferably utilize a titanium layer 88, 116 to maintain proper adhesion and electrical continuity between the silicon (amorphous or crystalline) and the sputtered iridium/iridium oxide layers 86, 118.

In one preferred embodiment of this invention, the top amorphous silicon microphotodetector layer 60 is approximately 4000 angstroms in thickness. The N-amorphous silicon (N+ a-Si:H) 80, 80A and P-amorphous silicon (P+ a-Si:H) 76, 76A layers are approximately 150 angstroms thick, while the thicker intrinsic-amorphous silicon (undoped a-Si:H) layer 78 in the middle is approximately 3600 angstroms. The thickness for the gain adjustment layer 100 is approximately 15 micrometer ($\mu$m) and the bottom side titanium layer 116 and iridium/iridium oxide layer 118 of the lower electrode 114 adding approximately 150 angstroms and 600 angstroms, respectively. One suitable size and configuration for each amorphous microphotodetector pixel 62 is an 11 $\mu$m by 11 $\mu$m square. In this configuration, each NiP 64A and PiN 63A segment is preferably 5.5 $\mu$m by 11 $\mu$m. This size and shape of each microphotodetector pixel 62 is preferable because the retinal stimulation electrode center-to-center spacing in the VGMMRI 10 then approaches the resolution pitch of the human retina. Because of the lower fill factor in each pixel 62 as the geometries of the pixel becomes smaller, more light flux is necessary to maintain a give current flux. The VGMMRI 10, however, can drive a current density more evenly through the retina by its ability to increase voltage and current gain for an entire area or for an individual pixel. The term fill factor refers to the area of each pixel "filled" by incoming light. The fill factor is proportional to the total amount of photoactive surface relative to the amount of the photoactive surface blocked by the stimulating electrode and any other structures.

The VGMMRI implant 10 may be used in an eye to treat an area of outer retina and/or limited inner retina dysfunction. The shape of the implant may be fabricated to resemble the shape of that area. Shapes such as a disk, an annular disk, a partial annular disk, or irregular shapes are useful and readily fabricated by one skilled in the art.

Figure 4A:
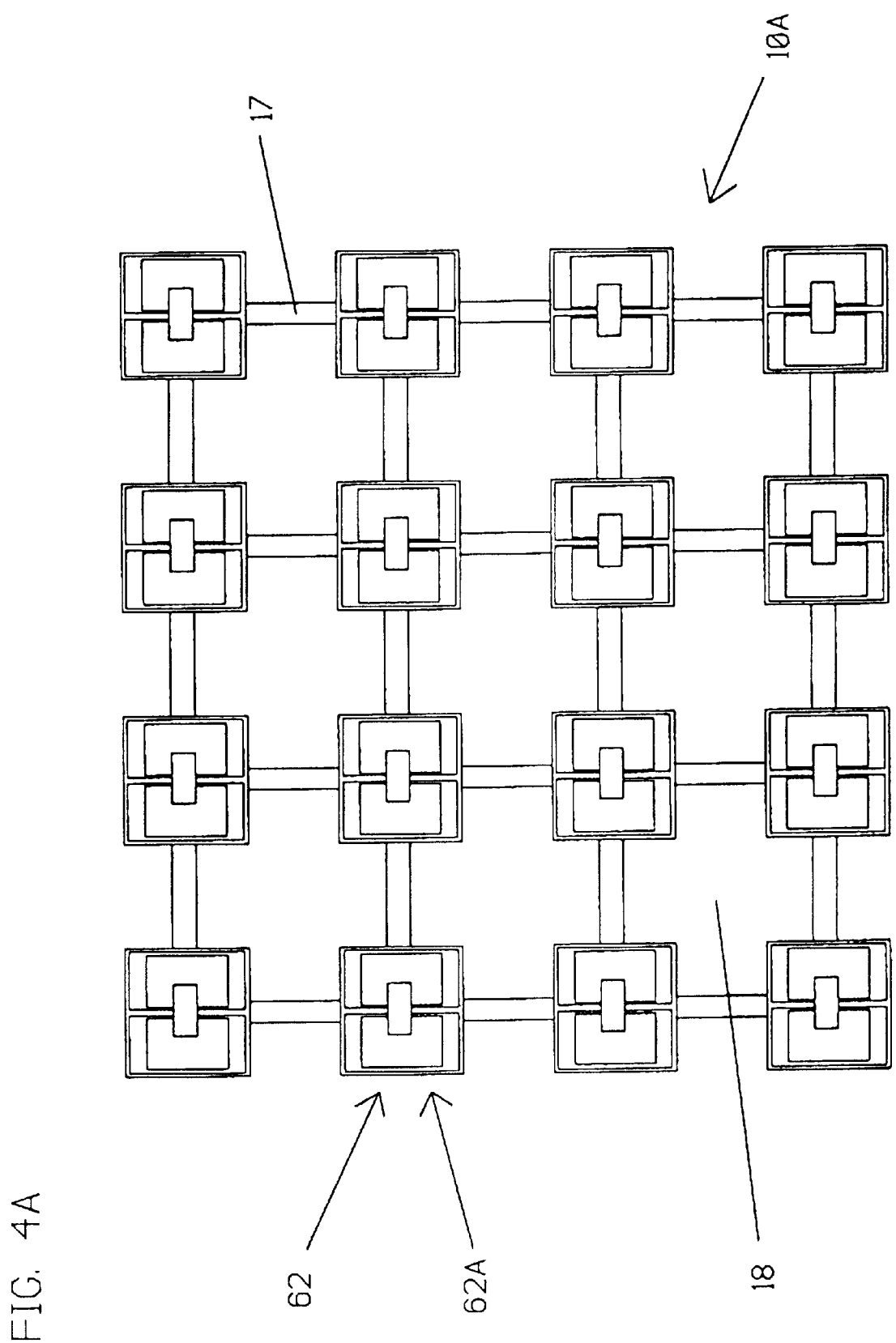
FIG. 4A is a plan view of another preferred embodiment of the VGMMRI wherein each microphotodetector pair with its gain adjustment layer is embedded in a lattice-like mesh and separated in space from each adjacent microphotodetector pair and its respective gain adjustment layer.

As shown in the plan view of FIG. 4A, in another preferred embodiment, the VGMMRI device 10A is fabricated as an array whose pixel blocks 62A are preferably comprised of 1 to 9 microphotodetector sub-pixels 62, in 1×1, 2×2 or 3×3 blocks, that are then plurally secured in an even pattern in a mesh-like lattice 17. The mesh-like lattice 17 is preferably made of a flexible biocompatible material such as silicon of Parylene. The embodiment of FIG. 4A shows 1×1 pixel blocks 62A. The openings 18 in the mesh-like lattice 17 allow nourishment, nutrients, oxygen, carbon dioxide, and other biological compounds to pass readily between the inner retina (neurosensory retina) and the outer retina (retinal pigment epithelium) and are beneficial to the retina. This mesh-like lattice 17 design thus aids the biocompatibility of the VGMMRI device. 10A.

Wafer Processing of VGMMRI Devices

Figure 5A:
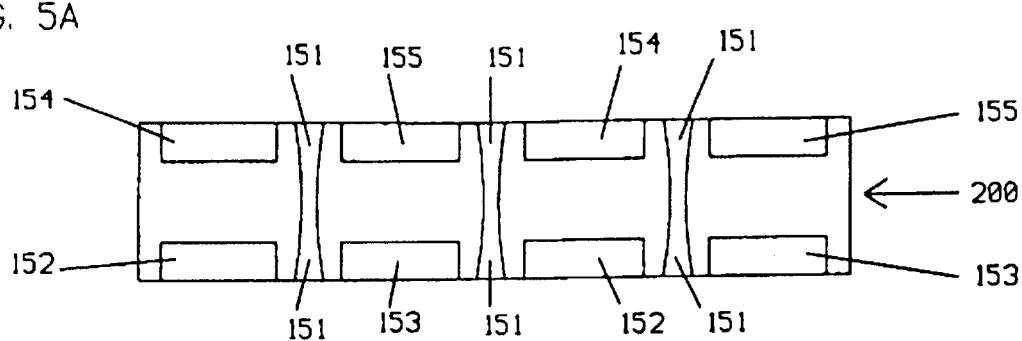
FIGS. 5A–5C illustrate the stages of fabrication for one preferred embodiment of the VGMMRI.
Figure 5B:
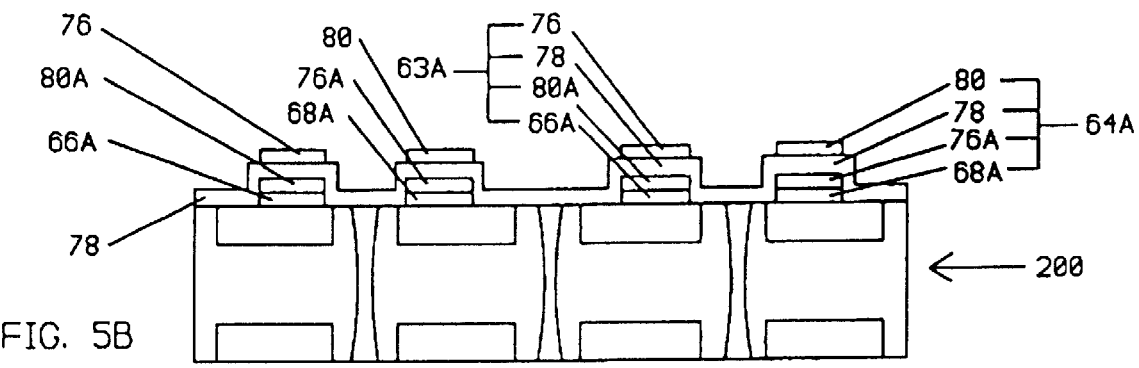
Figure 5C:
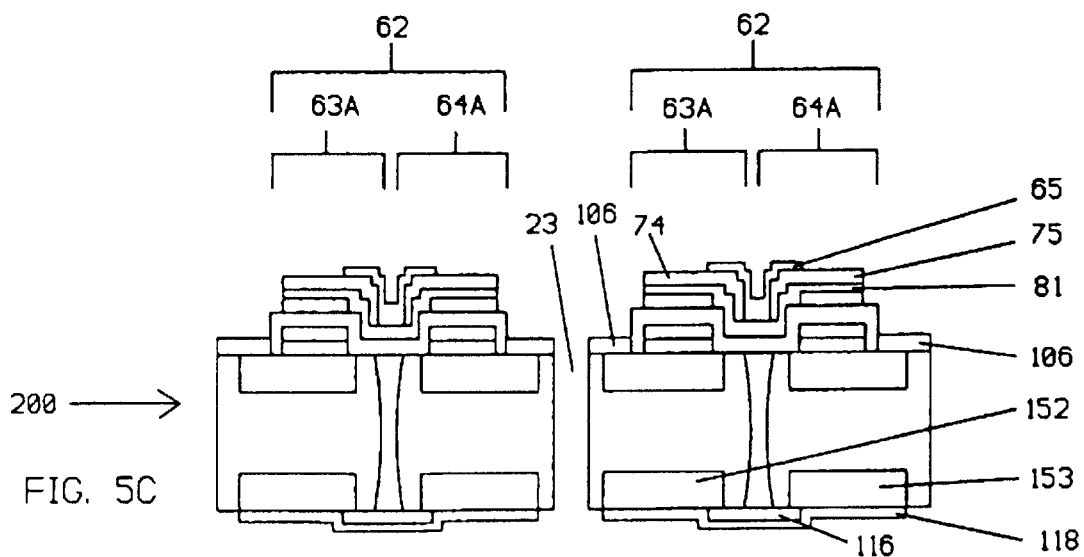

With reference to FIGS. 5A, 5B, and 5C, a VGMMRI is preferably fabricated using silicon on insulator (SOI) wafers known in the art. The top side is processed first, followed by a back etch of the support portion of the SOI wafer. This etch will automatically stop at the SOI oxide layer interface. Removal of this oxide layer will reveal the bottom side of the silicon membrane ready for further processing. The suitable thickness of the silicon membrane is from approximately 2 to 50 microns. Standard ion implantation and diffusion techniques are used to produce active regions on both sides of the silicon membrane.

FIG. 5A shows a portion of the silicon membrane 200 that is to be processed into two VGMMRI pixels with P+ active regions 154, 153 and N+ active regions 152, 155 with N+ channel stop regions 151 driven in from the top and bottom sides. The active regions on the bottom side have a complimentary pattern to that of the top side.

FIG. 5B shows continuation of the fabrication process with deposition approximately 50 angstroms of platinum over 50 angstroms of titanium for the base metal 66A, 68A, on the top side and patterning this metal layer 66A, 68A to form the foundation for the amorphous silicon layer. P+a-Si:H 76A is deposited to a thickness of approximately 150 angstroms on the top side and patterned to match the Pt/Ti pattern 68A only over the N+ regions 155 as shown in FIGS. 5A, 5B. Similarly, approximately 150 angstroms of N+a-Si:H 80A is deposited and patterned to match the Pt/Ti pattern 66A only over the P+ regions 154 as shown in FIGS. 5A, 5B. A sacrificial 0.1 micrometer thick protective aluminum layer, such as is commonly used in the art, is used to protect existing features whenever this is required in patterning.

Approximately 3700 angstroms of undoped a-Si:H 78 is then deposited over all features. This layer will become the intrinsic layer of the PiN and NiP microphotodiodes in the amorphous silicon side of the finished VGMMRI device. Continuing with FIG. 5B, approximately 100 angstroms of N+a-Si:H 80 is now deposited and patterned only over P+a-Si:H areas 76A. Similarly, approximately 100 angstroms of P+a-Si: H 76 is deposited and patterned over the N+a-Si:H 80A areas.

FIG. 5C shows the final stages in the fabrication of the VGMMRI pixels 62. The top transparent electrode 81 of each amorphous photodiode pixel 62 is fabricated by depositing approximately 50 angstroms of platinum over 50 angstroms of titanium and patterning the electrode 81 to match each PiN 63A and NiP 64A amorphous silicon structure of the pixel 62, also shown in FIG. 5B.

Continuing with FIG. 5C, the filters for the amorphous and crystalline PiN and NiP photodiodes are formed next. For clarity, the fabrication of filters over only one of the VGMMRI pixels 62 is described. To form the visible light pass filter, a protective aluminum mask layer is deposited on the top side and the aluminum is etched away over the PiN amorphous silicon microphotodiode 63A of FIG. 5C, and visible light pass dielectric filter material 74 is deposited and then patterned to remain only within these openings. The aluminum mask is now etched away and a fresh aluminum mask is deposited. In a similar fashion, the IR-A light pass filter 75 over the NiP amorphous silicon microphotodiode 64A is formed. After completing the visible light and IR-A pass filter layers 74, 75, a platinum layer of 0.5 micrometers is deposited and patterned on the amorphous silicon PiN/NiP electrode area to begin the formation of the electrode 65. The electrode 65 is completed by patterning, using photoresist lift-off, approximately 150 angstroms of platinum followed by approximately 600 angstroms of iridium/iridium oxide.

Referring again to FIG. 5C, the IR-B light pass dielectric filter layer 106 is now deposited and patterned over only the light facing portions of the crystalline silicon PiN and NiP photodiodes using the same aluminum protective layer process followed by selective etching and removal as already described.

As further shown in FIG. 5C, an insulation layer of silicon dioxide 116 is patterned between the bottom crystalline silicon P portion 153 and the bottom crystalline silicon N portion 152. Next, approximately 150 angstroms of titanium, followed by approximately 600 angstroms iridium/iridium oxide are deposited on the bottom side to form the rear electrode 118. This bottom electrode 118 of each VGMMRI pixel 62 can either be electrically isolated or electrically connected to the electrodes 118 of other VGM- MRI pixels 62, in the latter case to form a common ground electrode plane in another embodiment of the VGMMRI device. Finally, in FIG. 5C, a channel 23 is created between the VGMMRI pixels 62 using reactive ion etching that etches entirely through most to all of the intervening area of crystalline silicon substrate 200, IR-B filter 106, and back electrode 118. In the preferred embodiment where most but not all of the intervening crystalline silicon substrate 200 area is etched away, silicon bridges remain in some areas between the VGMMRI pixels 62. The VGMMRI pixels 62 are retained in position by the silicon bridges in this case. In a preferred embodiment where all of the intervening silicon area has been etched away, the VGMMRI pixels 62 are embedded in a lattice-like, flexible, biocompatible mesh that has been previously described.

Although both crystalline silicon and amorphous silicon is used in a preferred embodiment, amorphous silicon by itself, or crystalline silicon by itself, may be used to fabricate the VGMMRI device. In addition, as shown in FIG. 5C, although the same IR-B filter 106 is used in a preferred embodiment to cover the PiN and NiP gain photodiodes of the crystalline silicon, in other embodiments, different filters, each passing a different portion of IR-B light, are used to cover the PiN and NiP gain photodiodes respectively. These other embodiments provide greater control over the amount of voltage and current gain provided by the gain photodiodes by allowing individual wavelength portions of IR-B light to control the gain of the PiN or NiP gain photodiode.

Operation of the VGMMRI

As described above, an advantage of the disclosed VGM-MRI 10 in FIGS. 3–5 is that voltage and current gain of the VGMMRI 10 can be controlled. In one preferred embodiment, this gain is controllable for the entire implant 10 and useable by any of the microphotodetector pixels 62. When implanted in the subretinal space of the eye, the VGMMRI 10 receives the light of images implanted in the subretinal space. Photovoltaic potentials are generated at each pixel electrode 65 in proportion to the intensity of the incident light. These photovoltaic potentials are retinotopically disturbed in the shape of the incident images and produce charges at the iridium/iridium oxide electrodes 65 to the overlying retinal cells and structure 34 is both resistive and capacitive. Depending upon which of the microphotodetectors 63A, 64A of a pixel 62 is stimulated more strongly by the wavelengths of incident light, the charge developed at the electrode 65 is either positive or negative. A positive charge causes the contacting overlying cell structure 30, 32 of FIG. 2, to produce a sensation of darkness through depolarization of cell membranes, while a negative charge causes a sensation of light through hyperpolarization of cell membranes.

Although other electrode materials may be used, an advantage of the preferred iridium/iridium oxide electrode of this invention is that it supports better DC ionic flow into tissue in addition to having a higher capacitive effect than is possible with other electrode materials such as platinum. This results in lower work function for the VGMMRI 10 and thus the VGMMRI operates with lower electrode potentials. The lower electrode potentials result in better low light performance and lessen potential electrolysis damage to ocular tissues. Secondly, the larger capacitive effect of the preferred iridium/iridium electrode of the VGMMRI, 10 provides a passive charge balance effect to the tissues during capacitive discharge of the electrode during the moments when light is absent.

In some instances, the amount of light available at the VGMMRI 10 may be low, or the electric stimulation threshold of the retina overlying the implant may be high. In either case, additional voltage and/or current gain is necessary to stimulate the surviving cell layers and/or structures. The VGMMRI 10 embodiment of this invention achieves the desired gain by stacking two layers of microphotodetectors in series to achieve up to twice the voltage swing. The resultant higher voltage drives a higher current through the tissues.

As shown in FIG. 4 the amorphous microphotodetector pixel layer 60 is stacked onto the crystalline PiN/NiP microphotodetector strips 66A, 68A of the gain adjustment layer 100. The layers 60, 100 are stacked such that the pixels 62 and their respective PiN and NiP contact strips 66A, 68A in the gain adjustment layer 100 are connected in series with the underlying photodetectors 66, 68. Thus, twice the positive or negative voltage swing may be attainable as compared to the voltage swing attainable with just the single top PiN/NiP microphotodetector layer 60.

The filters 74, 75, 106 on the VGMMRI 10 allow for control of how much gain is obtained and where that gain is distributed by allowing different wavelengths of light to preferentially stimulate different microphotodetectors under each filter. Preferably, the filters 74, 75 and 106 are fabricated so that each of the three filters pass a different wavelength, or range of wavelengths of visible and/or infrared light. In one embodiment, the IR-A and IR-B filters 75, 106 are selected to pass a portion of wavelengths in the range of 400 nanometers to 2 microns. More preferably, the IR-B filters 106 are selected to pass a portion of wavelengths in the range of 800 nanometers to 2 microns and the IR-A filters 75 are selected to pass a portion of wavelengths in the range of 400 nanometers to 2 microns. The visible light pass filters 74 are preferably selected to pass a portion of wavelengths in the range of 400 nanometers to 2 microns, and more preferably in the range of 400 to 650 nanometers. The different wavelengths of light may enter the eye from the environment and/or from another external source such as the headset discussed below with respect to FIGS. 6 and 7.

For example, because the portions of the PiN and NiP strips 66, 68 of the gain adjustment layer 100 extending outside the perimeter of the pixel layer 60 are coated with the IR-B 106 filter, wavelengths that pass through the IR-B filter are used to selectively provide power to the gain layer 100 which in turn provides the additional voltage and current gain to the overlying microphotodetector layer 60. Both the PiN microphotodetectors 63A and the NiP microphotodetectors 64A may utilize this reservoir of power from the gain layer 100. The foregoing mechanism allows the microphotodetectors 63A and 64A to generate higher voltages and current than they would otherwise generate if not for the underlying gain layer 100.

Because one of the microphotodetectors 63A, 64A is more sensitive to visible light and the other more sensitive to IR-A light, respectively, light of these two predominant wavelengths will generate sensations of light and darkness in the overlying retinal layers; a positive potential at electrode 65 will produce a sensation of darkness, and a negative potential a sensation of light. This mechanism is described in greater detail in U.S. Pat. No. 6,230,057 and in U.S. Pat. No. 5,895,415, the disclosures of each are incorporated by reference herein.

In a preferred embodiment, as shown in FIGS. 3 and 4, the VGMMRI implant 10 has a rectangular microphotodetector pixel top layer 60 centered overlying a larger area gain adjustment layer 100 so that approximately 80% of the gain adjustment layer 100 is covered by layer 60 and the remaining 20% of layer 100 is exposed to incident light. Although only 20% of the gain adjustment layer 100 is exposed in this embodiment, smaller or larger percentages of exposed area may be fabricated in other embodiments.

In another embodiment, as shown in FIG. 4A, the VGM-MRI 10 has a gain adjustment layer integrated into each pixel 62 and both are physically separated in space from other pixels 62. This configuration allows individual VGM-MRI pixels 62 to be embedded, as shown, within a lattice-like mesh 17. The lattice-like mesh 17 is also configurable to have a common ground electrode for all the pixels 62.

Figure 6:
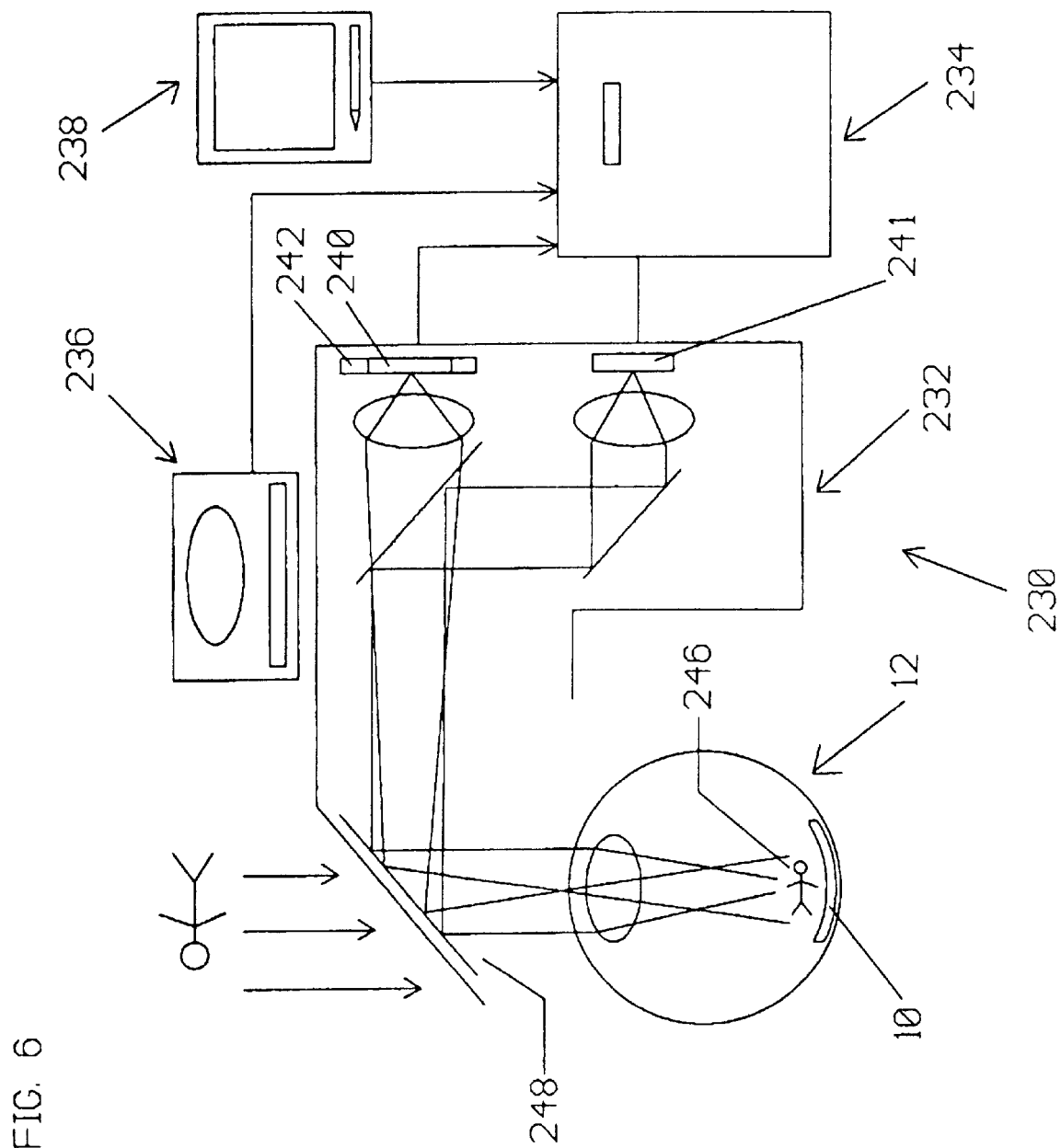
FIG. 6 is a generalized schematic diagram of a modified Adaptive Imaging Retinal Stimulation System (AIRES), capable of use with the VGMMRI of FIGS. 3, 4 and 4A.
Figure 7:
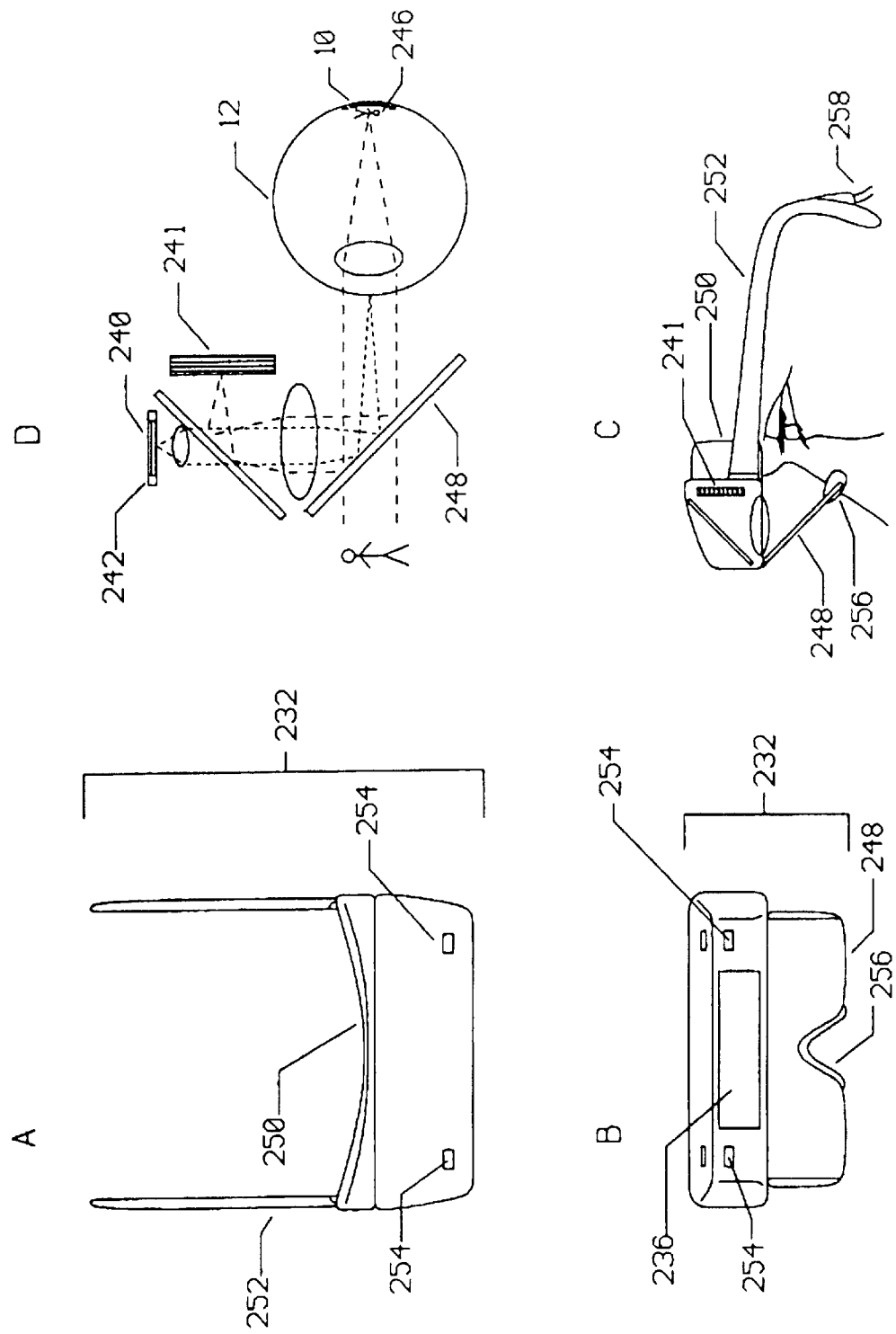
FIGS. 7 A–D show a modified PTOS device suitable for use in the AIRES system of FIG. 6.
Figure 8:
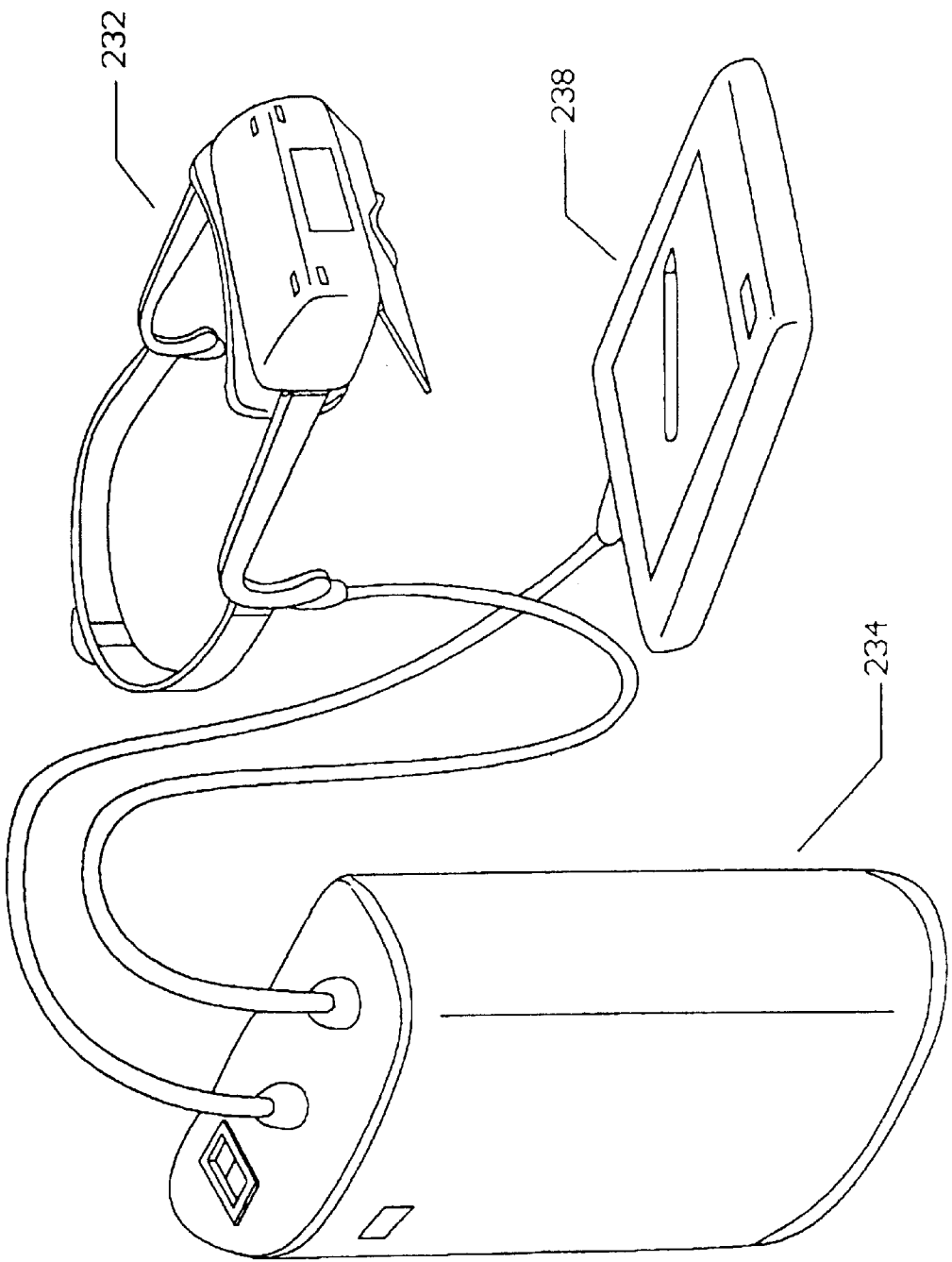
FIG. 8 shows the components of an alternative embodiment of the AIRES system of FIG. 6.

The visible, IR-A, and IR-B light power supply to the VGMMRI 10 is optionally provided by an external headset system in addition to the visible, IR-A, and IR-B provided by an external headset system in addition to the visible, headset system 230, the so-called AIRES-M system 230 of FIGS. 6, 7, 8, is a modification of the PTOS headset of the Adaptive Imaging Retinal Stimulation System (AIRES) of U.S. Pat. No. 5,895,415.

As shown in FIG. 6, the AIRES-M 230 includes component sub-systems of a Projection and Tracking Optical System (PTOS) headset 232, a Neuro-Net Computer (NNC) 234, an Imaging CCD Camera (IMCCD) 236 and an Input Stylus Pad (ISP) 238. A Pupil Reflex Tracking CCD (PRTCCD) 242 that has incorporated an IR-B LED display (IRBLED) 240, and a visible/IR-A LED display (VISIRALED) 241, are positoned inside the PTOS 232. A VGMMRI 10 is shown in the subretinal space of the eye 12. In operation, IR-A and visible light images form the VISIRALED 241 within the PTOS 232 are optically projected into the eye 12, when necessary, for example, during periods of low ambient lighting. IR-B Illumination from the IRBLED 240 is also projected into the eye when necessary to power the voltage and current gain of layer 100 from FIG. 4. Light intensity, duration, wavelength balance, and pulsing frequency of the VISIRALED 241 and IRBLED 240 is controlled by the NNC 234 and modulated by patient inputs via the interfaced ISP 238. The IMCCD 236, which is mounted on or in the PTOS headset 232, provide the image inputs to the NNC 234 which in turn programs the visible, IR-A, and IR-B outputs of the VISIRALED 241 and IRBLED 240. A PRTCCD 242 is integrated into the PTOS headset 232 to track eye movements via changes in the position of the pupillary Purkinje reflexes. The PRTCCD 242 outputs to the NNC 234 which in turn shifts the position of projected images from the VISIRALED 241 via electronic control to follow the eye movements. The PTOS 232 is also programmable to provide just diffuse IR-B illumination to the VGMMRI 10 without projecting visible or IR-A images.

The PTOS 232 is also programmable via the NNC 234 to project patterned IR-B light onto various VGMMRI pixels in the embodiment where the gain adjustment layer 100 is integrated into each of the VGMMRI pixels and the VGM-MRI pixels are separated in space and embedded in a lattice-like mesh.

FIGS. 7A–7D show a glasses-like configuration 232 of the PTOS component of the AIRES-M system 230 of FIG. 6. As seen in FIG. 7D, although the schematic of the optical system differs somewhat from the generalized schematic of the PTOS component 232 demonstrated in FIG. 6, the spirit and function of both versions of the devices are the same. FIG. 7A is a top view of the PTOS 232. It shows the headpad 250, the temple pieces 252, and the ambient light intensity sensors 254. FIG. 7B is a front view of the PTOS 232. It shows the external partially reflective/transmissive mirror 248, a supporting nose piece 256, ambient light intensity sensors 254, and the window for the IMCCD camera 236 shown in FIG. 6. FIG. 7C is a phantom side view of the PTOS 232. It shows an internal IR-A and visible light LED display light source 241. Also shown is the partially reflective/transmissive mirror 248, the supporting nose piece 256, the headpad 250, one of the temple pieces 252, and the power supply and signal wire cable 258 leading to the NNC 234 of FIG. 6. FIG. 7D shows the VGMMRI 10 disposed in the subretinal space of the eye 12 with a focused image 246. It also shows the internal visible light/IR-A LED display light source 241, the PRTCCD 242, the IRBLED 240 and the external partially reflective/transmissive mirror 248. FIG. 8 shows the components of the AIRES-M system, consisting of the PTOS 232, the portable NNC 234 which may be secured to the patient's body, and the ISP 238 input device.

C. Implantation of the VGMMRI into the Eye

Figure 9:
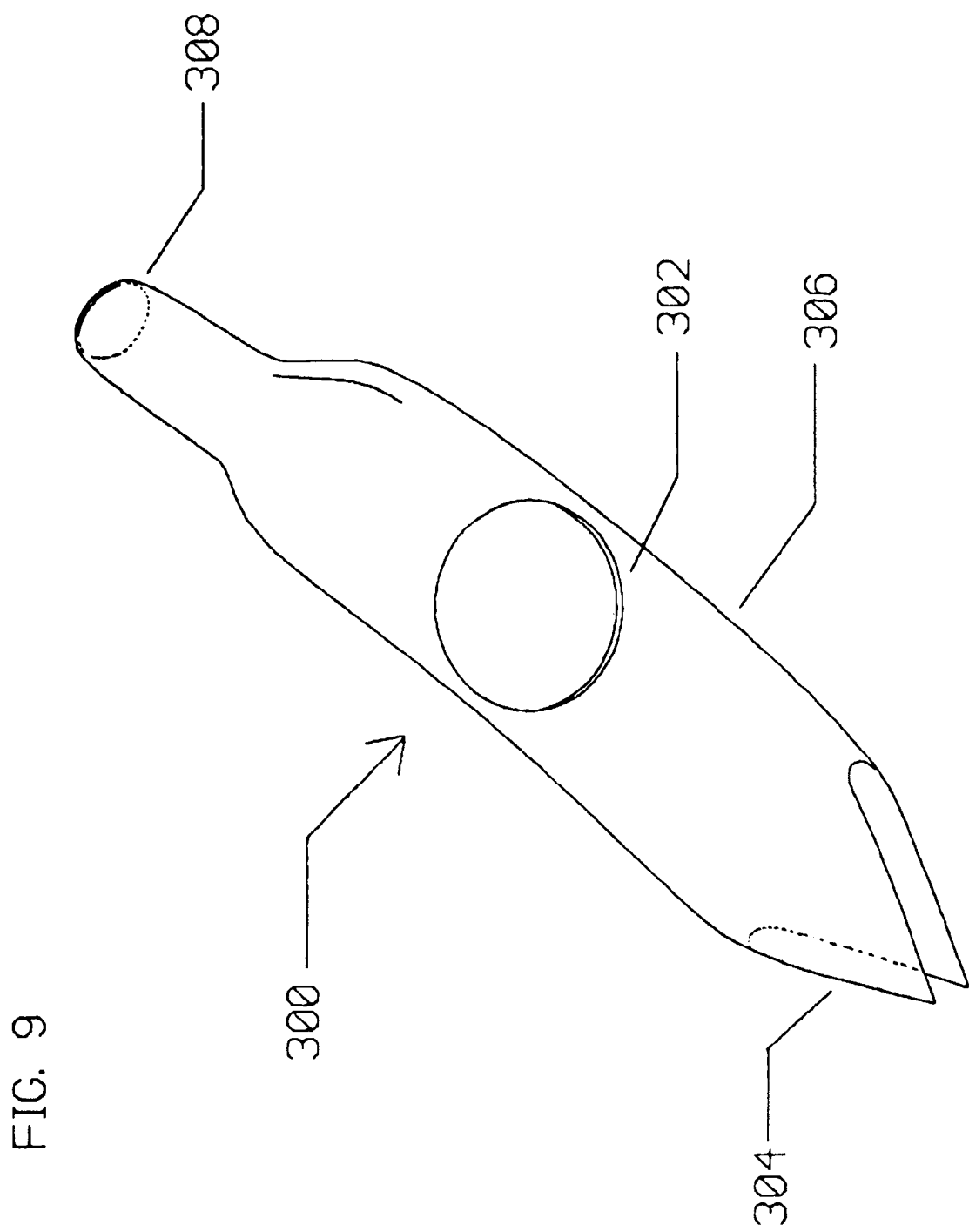
FIG. 9 is a perspective view of a retinal implant injector (RII) for use in implanting a retinal implant such as the VGMMRI of FIGS. 3, 4, 4A, and 5A–5C.

As shown in FIG. 9, a retinal implant injector (RII) 300 may be used to place a retinal implant 302 into the vitreous cavity of the eye, or to place a retinal implant 302 directly into the subretinal space of the eye. The RII 300 employs a fluid, which is placed inside the RII 300, to push the retinal implant 302 to its exit at the terminal tip 304 of the RII 300. By this means, controlled deposition of the retinal implant 302 is possible without physically having to hold the retinal implant 302 with an instrument that can cause damage to the implant 302.

Figure 10:
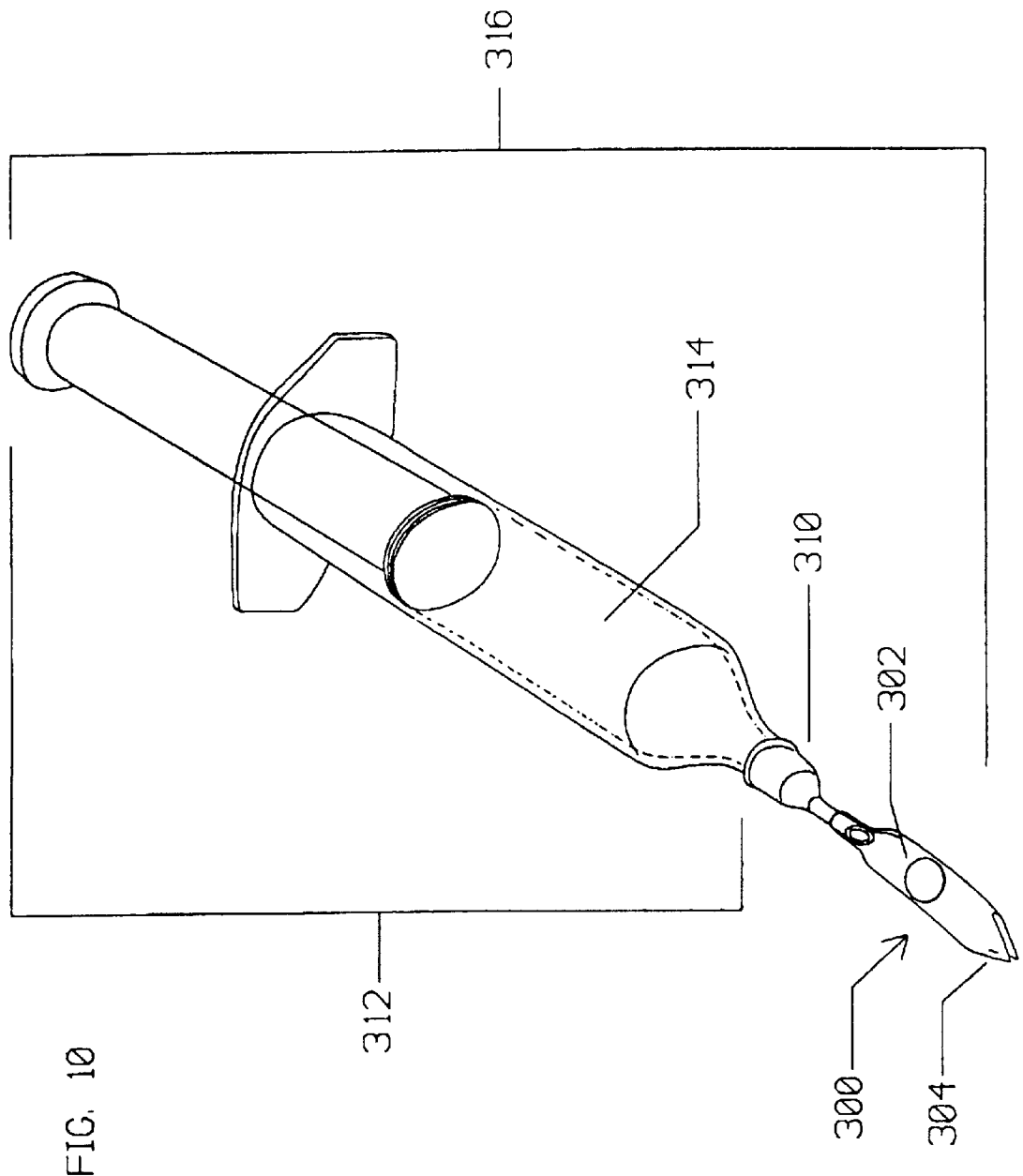
FIG. 10 is a perspective view of a syringe retinal implant injector (SRI) assembly comprising the RII of FIG. 9 with a retinal implant inside, an attached cannula, and an attached operator controlled fluid filled syringe.

Also shown in FIG. 9, the RII 300 is fabricated from tubing which is preferably made of Teflon (polytetrafluoroethylene) or Parylene and is transparent. It is flattened through most of its length with a taper 304 at the tip of its flattened end. The flattened cross-section 306 preferably is similar to the cross-section of the retinal implant 302. The opposite end of the tube maintains a round cross-section 308 that allows the RII 300 to be inserted around a cannula 310 as shown in FIG. 10, that in turn is attached to a syringe 312 containing the fluid 314 used for the injection. The injection fluid 314 is any biocompatible fluid but is preferably saline or a viscoelastic material.

As shown in FIG. 10, in use, the retinal implant 302 is first placed within the RII 300. The RII 300 is then attached around a cannula 310 that in turn is attached to a syringe 312 containing the preferred saline or viscoelastic fluid. The entire Retinal Injector Assembly 316 is held by the operator via the syringe 312. The tapered tip 304 of the RII 300 is then advanced into the vitreous cavity of the eye through an opening made through the eye wall for this purpose. Once the tip 304 of the RII 300 is placed into position within the vitreous cavity and next to the retinotomy incision made through the retina, the retinal implant 302 is pushed out of the RII 300 by fluid pressure exerted by operation of the fluid filled syringe 312 from outside the eye. The retinal implant is then manipulated with surgical instruments either to a position underneath the retina in the subretinal space, or on top of the retina in the epiretinal position. The RII 300 is also useable to directly inject the retinal implant 302 through the retinotomy opening into the subretinal space. In this case, the tip 304 of the RII 300 is placed directly into the retinotomy opening before injection of the retinal implant 302.

Figure 11:
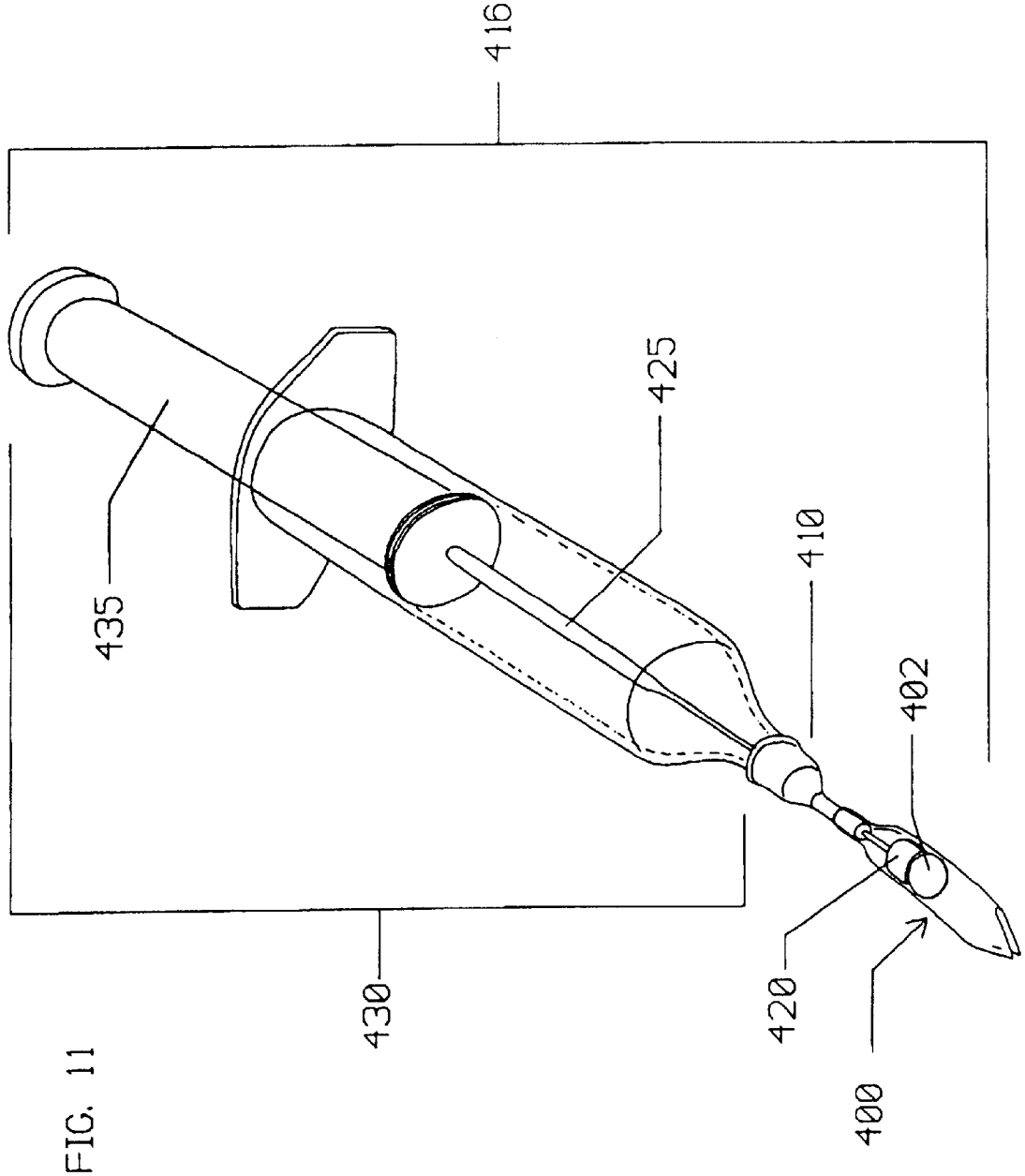
FIG. 11 is a perspective view of an alternative embodiment of the SRI of FIG. 10.

In another embodiment, as shown in FIG. 11, a RII-1 injector assembly 416 utilizes an injector plunger 420, placed within the injector 400, to push the implant 402 out of the injector 400. The injector plunger 420 is shaped to conform to the inside cross-section of the injector 400 and is attached to any variety of well-known methods of moving the plunger 420 forward. In the preferred embodiment, a rod-like extension 425 connects the injector plunger 420 to the syringe plunger 435 of a syringe 430. Pushing the syringe plunger 435 thus pushes the injector plunger 420 forward and moves the implant 402 out of the injector 400.

From the foregoing, a VGMMRI retinal implant having a multilayer structure of PiN and NiP microphotodiode pairs is disclosed in a structure allowing for voltage and current gain adjustment. In a preferred embodiment, the VGMMRI microphotodetector pixel structure is rectangular, although a round shape or other shapes may be implemented for the VGMMRI microphotodetector pixel structure, and easily fabricated by one ordinarily skilled in the art. In another preferred embodiment, the VGMMRI microphotodetector pixels are fabricated as individual units separated in space and embedded in a lattice-like mesh. The mesh may also have a common conductor that contacts all the ground electrodes of the microphotodetector pixels on the mesh, providing a common ground plane.

It is intended that foregoing detailed description should be regarded as illustrative rather than limiting, and that it be understood that the following claims, including all equivalents are intended to define the scope of this invention.

We claim:

1. A retinal implant for electrically inducing formed vision in an eye, the retinal implant comprising:
   a plurality of first layer microphotodetector pairs for receiving light incident on the eye, each first layer microphotodetector pair comprising:
   a PiN microphotodetector and a NiP microphotodetector, wherein the P-portion of the PiN microphotodetector and the N-portion of the NiP microphotodetector are aligned on a first end, and the N-portion of the piN microphotodetector and the P-portion of the NiP microphotodetector are aligned on a second end; and
   a common electrode in electrical communication between the P-portion and the N-portion of the first end of the microphotodetector pair;
   a gain adjustment layer having a first side and a second side, the first side having a first portion electrically connected in series with the second end of at least a portion of the plurality of first layer microphotodetector pairs, and a second portion integrally formed with the first portion and extending away from the first portion, wherein the second portion is oriented to receive light incident on the eye; and,
   a common electrode plane in electrical contact with the second side of the gain adjustment layer, whereby the common electrode plane serves as an electrical ground for the retinal implant.

2. The retinal implant of claim 1, wherein the gain adjustment layer comprises at least one PiN photodetector having a P-portion and an N-portion, the P-portion of the at least one PiN photodetector of the gain adjustment layer in electrical communication with the N-portion of at least one of the PiN microphotodetectors of the first layer microphotodetector pairs.

3. The retinal implant of claim 1, wherein the gain adjustment layer comprises at least one NiP photodetector having a N-portion and a P-portion, the N-portion of the at least one NiP photodetector in electrical communication with the P-portion of at least one of the first layer NiP microphotodetectors of the first layer microphotodetector pairs.

4. The retinal implant of claim 1, wherein the gain adjustment layer comprises a plurality of parallel PiN and NiP photodetector strips.

5. The retinal implant of claim 4, wherein the plurality of first layer microphotodetector pairs further comprises columns of microphotodetector pairs, wherein the N-portion of the PiN microphotodetector in a pair is in electrical communication with a P-portion of a PiN photodetector strip in the gain layer and the P-portion of the NiP microphotodetector in the pair is in electrical communication with a N-portion of a NiP photodetector strip in the gain layer.

6. The retinal implant of claim 4, wherein the plurality of parallel PiN and NiP photodetector strips are positioned in an alternating pattern.

7. The retinal implant of claim 1, wherein the first end of the second portion of the gain adjustment layer is coated with a first filter material configured to pass a first predetermined portion of wavelengths of visible and infrared light selected from a range of 400 nanometers to 2 microns.

8. The retinal implant of claim 7, wherein the first predetermined portion of wavelengths is selected from a range of 800 nanometers to 2 microns.

9. The retinal implant of claim 7, wherein each of the plurality of first layer microphotodetector pairs further comprises a second filter material positioned over the N-portion on the first end of at least one of the plurality of microphotodetector pairs.

10. The retinal implant of claim 9, wherein the second filter material is configured to pass a second predetermined portion of wavelengths of visible or infrared light in a range of 400 nanometers to 2 microns.

11. The retinal implant of claim 10 wherein the second predetermined portion of wavelengths is different than the first predetermined portion of wavelengths.

12. The retinal implant of claim 11 wherein the second predetermined portion of wavelengths is selected from a range of 650 nanometers to 800 nanometers.

13. The retinal implant according to any of claims 7–11 wherein each of the plurality of first layer microphotodetector pairs further comprises a third filter material positioned over the P-portion on the first end of at least one of the plurality of microphotodetector pairs.

14. The retinal implant of claim 13, wherein the third filter material is configured to pass a third predetermined portion of wavelengths selected from a range of 400 nanometers to 2 microns.

15. The retinal implant of claim 14 wherein the third predetermined portion of wavelengths is different than the first and second predetermined portions of wavelengths.

16. The retinal implant of claim 15, wherein the third predetermined portion of wavelengths is selected from a range of 400 nanometers to 650 nanometers.

17. A retinal implant for electrically inducing formed vision in an eye, the retinal implant comprising:
   a plurality of microphotodetector pixels, each of the plurality of microphotodetector pixels spaced apart from any adjacent microphotodetector pixels and each of the pixels embedded in a lattice-like mesh, wherein each of the microphotodetector pixels comprises:
   at least one first layer microphotodetector pair for receiving light incident on the eye, each microphotodetector pair comprising:
   a PiN microphotodetector and a NiP microphotodetector, wherein the P-portion of the PiN microphotodetector and the N-portion of the NiP microphotodetector are aligned on a first end, and the N-portion of the PiN microphotodetector and the P-portion of the NiP microphotodetector are aligned on a second end; and
   a common electrode in electrical communication between the P-portion and the N-portion of the first end of the microphotodetector pair; and a gain adjustment layer having a first side and a second side, the first side having a first portion electrically connected in series with the second end of at least a portion of the plurality of first layer microphotodetector pairs, and a second portion integrally formed with the first portion and extending away from the first portion, wherein the second portion is oriented to receive light incident on the eye.

18. The retinal implant of claim 17 wherein the lattice-like mesh comprises a common ground electrode electrically connected to all of the plurality of microphotodetector pixels.

19. A retinal implant for electrically inducing formed vision in an eye, the retinal implant comprising:

a first layer comprising a plurality of microphotodetector pairs, each microphotodetector pair comprising:

a PiN microphotodetector and a NiP microphotodetector, wherein the P-portion of the PiN microphotodetector and the N-portion of the NiP microphotodetector are aligned on a first end, and the N-portion of the PiN microphotodetector and the P-portion of the NiP microphotodetector are aligned on a second end; and a common electrode in electrical communication between the P-portion and the N-portion of the first end of the microphotodetector pair;

a first common electrode strip in electrical contact with the N-portions of the second end of each of the plurality of PiN microphotodetectors of the microphotodetector pairs;

a second common electrode strip in electrical contact with the P-portions of the second end of each of the plurality of NiP microphotodetectors of the PiN/NiP microphotodetector pairs;

a second layer photodetector gain adjustment layer comprising a first end and a second end, the first end comprising a first portion electrically connected in series with the common electrode strips of both the N-portion and P-portion of the second end of the first layer of microphotodetector pairs, and a second portion integrally formed with the first portion extending away from the first portion and oriented to receive light incident on the eye; and a common electrode plane for the second layer photodetector gain adjustment layer in direct electrical contact with the second end of both the first portion and the second portion of the photodetector, gain adjustment layer, the common electrode plane serving as the electrical ground of the retinal implant.

20. An adjustable voltage and current gain microphotodetector retinal implant for electrically inducing formed vision in an eye, the retinal implant comprising:

a first microphotodetector layer comprising at least one PiN microphotodetector, the first microphotodetector layer having a bandpass filter configured to pass visible light, and a voltage and current gain adjustment layer comprising at least one PiN photodetector, the voltage and current gain adjustment layer having a first side comprising a first portion electrically connected in series with, and covered by, a portion of the at least one PiN microphotodetector of the first microphotodetector layer, and a second portion, not covered by the first microphotodetector layer, comprising an infrared bandpass filter.

21. The retinal implant of claim 20, further comprising at least one upper electrode positioned on the first microphotodetector layer, and at least one lower electrode positioned on the voltage and current gain adjustment layer, the upper and lower electrodes comprising sputtered iridium/iridium oxide.

22. An adjustable voltage and current gain microphotodetector retinal implant for electrically inducing formed vision in an eye, the retinal implant comprising:

a first microphotodetector layer comprising at least one PiN microphotodetector, the first microphotodetector layer comprising an amorphous silicon material, wherein the first microphotodetector layer is oriented to receive light incident on the eye; and a gain adjustment layer comprising at least on PiN photodetector, the PiN photodetector having a first side electrically connected in series with, and covered by, the at least one PiN microphotodetector of the first microphotodetector layer.

23. The retinal implant of claim 22, wherein the first microphotodetector layer is configured to pass a portion of the light incident on the eye and the first side of the at least one PiN photodetector of the gain adjustment layer receives the portion of light through the first microphotodetector layer.

* * * * *

UNITED STATES PATENT AND TRADEMARK OFFICE
CERTIFICATE OF CORRECTION

PATENT NO. : 6,389,317 B1
DATED : May 14, 2002
INVENTOR(S) : Vincent Chow et al.

It is certified that error appears in the above-identified patent and that said Letters Patent is hereby corrected as shown below:

<u>Title page,</u>
Item [56], OTHER PUBLICATIONS, delete "Observatios" and substitute
-- Observations -- in its place.
"Hagins, W.A., ..." reference delete "19:" and substitute -- 10: -- in its place.

<u>Column 18,</u>
Line 1, immediately after "photodetector" delete "," (comma).
Line 35, delete "at least on" and substitute -- at least one --
in its place.

Signed and Sealed this

Twenty-ninth Day of October, 2002

Attest:

Attesting Officer

JAMES E. ROGAN
*Director of the United States Patent and Trademark Office*